United States Patent
Almansour

(10) Patent No.: US 11,857,621 B2
(45) Date of Patent: Jan. 2, 2024

(54) SYNTHETIC PDNA VACCINES AGAINST COVID-19

(71) Applicant: Imam Abdulrahman Bin Faisal University, Dammam (SA)

(72) Inventor: Iman Almansour, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 182 days.

(21) Appl. No.: 17/323,357

(22) Filed: May 18, 2021

(65) Prior Publication Data

US 2022/0370596 A1 Nov. 24, 2022

(51) Int. Cl.
| | | |
|---|---|---|
| *A61K 39/215* | (2006.01) | |
| *C07K 14/005* | (2006.01) | |
| *A61P 31/14* | (2006.01) | |
| *A61K 9/00* | (2006.01) | |
| *A61K 39/00* | (2006.01) | |

(52) U.S. Cl.
CPC .......... *A61K 39/215* (2013.01); *A61K 9/0019* (2013.01); *A61P 31/14* (2018.01); *C07K 14/005* (2013.01); *A61K 2039/53* (2013.01); *A61K 2039/54* (2013.01); *A61K 2039/545* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

FOREIGN PATENT DOCUMENTS

| CN | 110951756 A | 4/2020 |
|---|---|---|
| CN | 111606981 A | 9/2020 |
| CN | 111671890 A | 9/2020 |
| RU | 2 720 614 C1 | 5/2020 |

OTHER PUBLICATIONS

Yu J, et al. DNA vaccine protection against SARS-CoV-2 in rhesus macaques. Science. Aug. 14, 2020;369(6505):806-811. And Supplementary Materials.*
Sharp PM, Li WH. The codon Adaptation Index—a measure of directional synonymous codon usage bias, and its potential applications. Nucleic Acids Res. Feb. 11, 1987;15(3): 1281-95, p. 1281.*
PcDNA3.1+ Mammalian Expression Vector. Thermo Fisher. https://www.thermofisher.com/order/catalog/product/V79020. 6-page printout. Accessed Jan. 11, 2023.*
MW 560963.1 Alignment with SEQ ID No. 1. Nucleotide BLAST. Accessed Jan. 11, 2023.*
Yu, et al. ; DNA vaccine protection against SARS-CoV-2 in rhesus macaques ; Science 369 ; pp. 806-811 ; Aug. 14, 2020 ; 8 Pages.
Smith, et al. ; Immunogenicity of a DNA vaccine candidate for COVID-19 ; Nature Communications 2020 ; 13 Pages.
Hayashi, et al. ; Preclinical study of DNA vaccines targeting SARS-CoV-2 ; bioRxiv reprint ; Oct. 21, 2020 ; 33 Pages.
Seo, et al. ; Soluble Spike DNA vaccine provides long-term protective immunity against SAR-CoV-2 in mice and nonhuman primates ; bioRxiv ; Oct. 10, 2020 ; 31 Pages.
Routhu, et al. ; Modified Vaccinia Ankara Based SARS-CoV-2 Vaccine Expressing Full-Length Spike Induces Strong Neutralizing Antibody Response ; bioRxiv ; Jun. 27, 2020 ; 19 Pages.
Almansour, et al ; Immunogenicity of Multiple Doses of pDNA Vaccines against SARS-CoV-2 ; Pharmaceuticals 2021, 14 ; 9 Pages.

* cited by examiner

*Primary Examiner* — Benjamin P Blumel
*Assistant Examiner* — Jeffrey Mark Sifford
(74) *Attorney, Agent, or Firm* — Oblon, McClelland, Maier & Neustadt, L.L.P.

(57) ABSTRACT

A pDNA-based vaccine against SARS-CoV-2 and methods for preventing or treating COVID-19 using it. The pDNA-vaccine encodes an immunogenic portion of SARS-CoV S1 protein, such as that encoded by SEQ ID NO: 1 or a fragment thereof, and may be conveniently administered intramuscularly without the need for electroporation or use of a gene gun.

18 Claims, 12 Drawing Sheets

Specification includes a Sequence Listing.

Fig. 3A

| Groups | Doses | Vaccines |
|---|---|---|
| 1 | Three | S.opt.FL pDNA |
| 2 | Four | S.opt.FL pDNA |
| 3 | Three | S1.opt pDNA |
| 4 | Four | S1.opt pDNA |
| 5 | Three | S.opt.FL + S1.opt pDNA |
| 6 | Four | S.opt.FL + S1.opt pDNA |
| 7 | Four | Control |

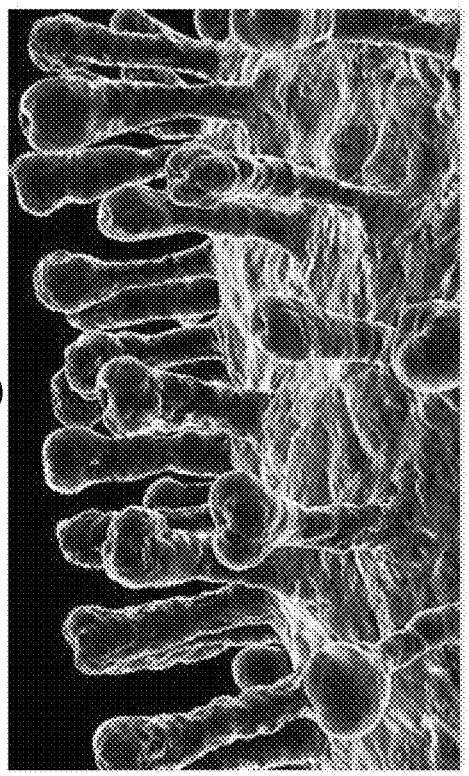
Fig. 7
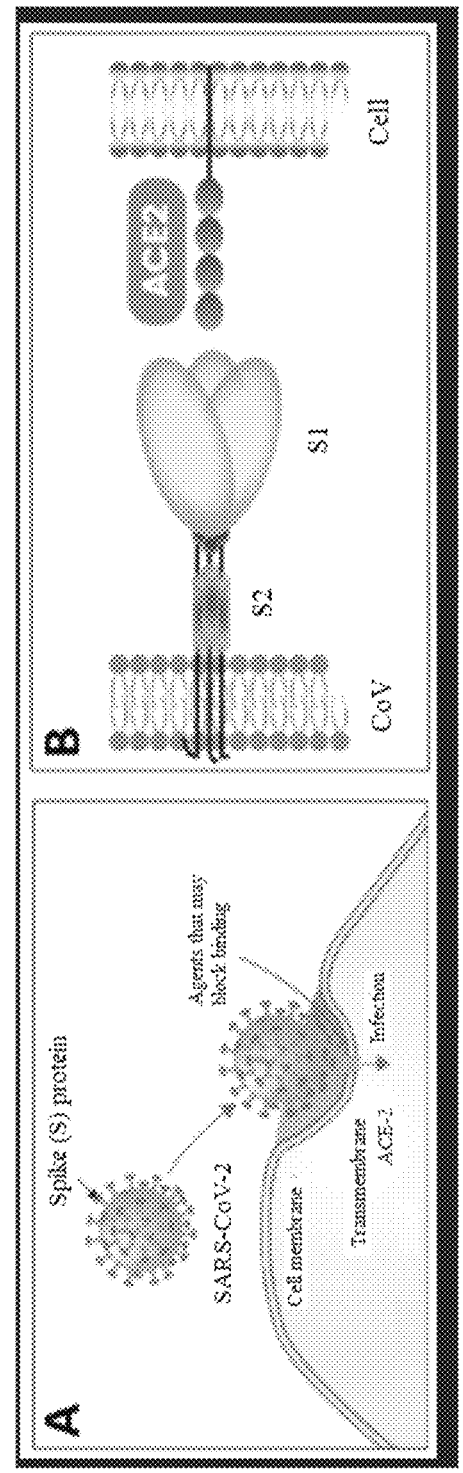
Fig. 8A
Fig. 8B

SEQUENCE LISTING

```
<160> NUMBER OF SEQ ID NOS: 7

<210> SEQ ID NO 1
<211> LENGTH: 3840
<212> TYPE: DNA
<213> ORGANISM: Artificial Sequence
<220> FEATURE:
<223> OTHER INFORMATION: Gene insert: S.opt.FL

<400> SEQUENCE: 1
gctagcgcca ccatgtttgt ctttctggtc ctgctgcctc tggtgtcatc tcagtgcgtg      60
aacctgacta ctagaactca gctgccccct gcttatacta attccttcac ccggggcgtg     120
tactatcctg acaaggtgtt tagaagctcc gtgctgcact ctacacagga tctgtttctg     180
ccattcttta gcaacgtgac ctggttccac gccatccacg tgagcggcac caatggcaca     240
aagcggttcg acaatcccgt gctgcctttt aacgatggcg tgtacttcgc ctctaccgag     300
aagagcaaca tcatcagagg ctggatcttt ggcaccacac tggactccaa gacacagtct     360
ctgctgatcg tgaacaatgc caccaacgtg gtcatcaagg tgtgcgagtt ccagttttgt     420
aatgatccct tcctgggcgt gtactatcac aagaacaata agagctggat ggagtccgag     480
tttagagtgt attctagcgc caacaattgc acatttgagt acgtgtccca gcctttcctg     540
atggacctgg agggcaagca gggcaatttc aagaacctga gggagttcgt gtttaagaat     600
atcgatggct acttcaaaat ctacagcaag cacaccccca tcaacctggt gcgcgacctg     660
cctcagggct tcagcgccct ggagcccctg gtggatctgc ctatcggcat caacatcacc     720
cggtttcaga cactgctggc cctgcacaga agctacctga cacccggcga ctcctctagc     780
ggatggaccg caggagctgc cgcctactat gtgggctatc tgcagccccg gaccttcctg     840
ctgaagtaca cgagaatgg caccatcaca gacgcagtgg attgcgccct ggacccctg      900 agcgagacaa agtgtacact gaagtccttt accgtggaga agggcatcta tcagacatcc     960
aatttcaggg tgcagccaac cgagtctatc gtgcgctttc ctaatatcac aaacctgtgc    1020
ccatttggcg aggtgttcaa cgcaaccagg ttcgccagcg tgtacgcatg gaataggaag    1080
cgcatctcta actgcgtggc cgactatagc gtgctgtaca actccgcctc tttcagcacc    1140
tttaagtgct atggcgtgtc ccccacaaag ctgaatgacc tgtgctttac caacgtgtac    1200
gccgattctt tcgtgatcag gggcgacgag gtgcgccaga tcgcacctgg acagacaggc    1260
aagatcgccg actacaatta taagctgcca gacgatttca ccggctgcgt gatcgcctgg    1320
aacagcaaca atctggattc caaggtcggc ggcaactaca attatctgta ccggctgttt    1380
```

```
agaaagagca atctgaagcc cttcgagagg gacatctcta cagaaatcta ccaggccggc    1440
agcacccctt gcaatggcgt ggagggcttt aactgttatt tcccactgca gtcctacggc    1500
ttccagccca caaacggcgt gggctatcag ccttaccgcg tggtggtgct gagctttgag    1560
ctgctgcacg caccagcaac agtgtgcgga cccaagaagt ccaccaatct ggtgaagaac    1620
aagtgcgtga acttcaactt caacggcctg accggcacag gcgtgctgac cgagtccaac    1680
aagaagttcc tgccatttca gcagttcggc agggacatcg cagataccac agacgccgtg    1740
cgcgacccac agaccctgga gatcctggac atcacaccct gctctttcgg cggcgtgagc    1800
gtgatcacac caggcaccaa tacaagcaac caggtggccg tgctgtatca ggacgtgaat    1860
tgtaccgagg tgcctgtggc catccacgcc gatcagctga ccccaacatg gcgggtgtac    1920
agcaccggct ccaacgtgtt ccagacaaga gccggatgcc tgatcggagc agagcacgtg    1980
aacaattcct atgagtgcga catcccaatc ggcgccggca tctgtgcctc ttaccagacc    2040
cagacaaact ctcccagaag agcccggagc gtggcctccc agtctatcat cgcctatacc    2100
atgtccctgg gcgccgagaa cagcgtggcc tactctaaca atagcatcgc catcccaacc    2160
aacttcacaa tctctgtgac cacagagatc ctgcccgtgt ccatgaccaa gacatctgtg    2220
gactgcacaa tgtatatctg tggcgattct accgagtgca gcaacctgct gctgcagtac    2280
ggcagctttt gtacccagct gaatagagcc ctgacaggca tcgccgtgga gcaggataag    2340
aacacacagg aggtgttcgc ccaggtgaag caaatctaca agaccccccc tatcaaggac    2400
tttggcggct tcaattttc ccagatcctg cctgatccat ccaagccttc taagcggagc    2460
tttatcgagg acctgctgtt caacaaggtg accctggccg atgccggctt catcaagcag    2520
tatggcgatt gcctgggcga catcgcagcc cgggacctga tctgcgccca gaagtttaat    2580
ggcctgaccg tgctgccacc cctgctgaca gatgagatga tcgcacagta cacaagcgcc    2640
ctgctggccg gcaccatcac atccggatgg accttcggcg caggagccgc cctgcagatc    2700
cccttttgcc tgcagatggc ctataggttc aacggcatcg gcgtgaccca gaatgtgctg    2760
tacgagaacc agaagctgat cgccaatcag tttaactccg ccatcggcaa gatccaggac    2820
agcctgtcct ctacagcctc cgccctgggc aagctgcagg atgtggtgaa tcagaacgcc    2880
caggccctga ataccctggt gaagcagctg agcagcaact tcggcgccat ctctagcgtg    2940
ctgaatgaca tcctgagccg gctggacaag gtggaggcag aggtgcagat cgaccggctg    3000
atcacaggca gactgcagtc tctgcagacc tatgtgacac agcagctgat cagggcagca    3060
gagatcaggg ccagcgccaa tctggcagca accaagatgt ccgagtgcgt gctgggccag    3120
tctaagagag tggacttttg tggcaagggc tatcacctga tgtccttccc tcagtctgcc    3180
ccacacggcg tggtgtttct gcacgtgacc tacgtgcccg cccaggagaa gaacttcacc    3240
acagcccctg ccatctgcca cgatggcaag gcccactttc caagggaggg cgtgttcgtg    3300
tccaacggca cccactggtt tgtgacacag cgcaatttct acgagcccca gatcatcacc    3360
acagacaata ccttcgtgag cggcaactgt gacgtggtca tcggcatcgt gaacaatacc    3420
gtgtatgatc cactgcagcc cgagctggac agctttaagg aggagctgga taagtacttc    3480
aagaatcaca cctcccctga cgtggatctg ggcgacatca gcggcatcaa tgcctccgtg    3540
gtgaacatcc agaaggagat cgaccgcctg aacgaggtgg ccaagaatct gaacgagagc    3600
ctgatcgatc tgcaggagct gggcaagtat gagcagtaca tcaagtggcc ctggtacatc    3660
tggctgggct tcatcgccgg cctgatcgcc atcgtgatgg tgaccatcat gctgtgctgt    3720
atgacatcct gctgttcttg cctgaagggc tgctgtagct gtggctcctg ctgtaagttt    3780
```
gatgaagatg atagtgaacc cgtgctgaaa ggcgtgaagc tgcattacac ctgaggatcc    3840

<210> SEQ ID NO 2
<211> LENGTH: 9231
<212> TYPE: DNA
<213> ORGANISM: Artificial Sequence
<220> FEATURE:
<223> OTHER INFORMATION: S.opt.FL pcDN1 (3.1) construct sequence

<400> SEQUENCE: 2

```
gacggatcgg gagatctccc gatccccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gccaccatgt ttgtctttct ggtcctgctg cctctggtgt catctcagtg cgtgaacctg     960
actactagaa ctcagctgcc ccctgcttat actaattcct tcacccgggg cgtgtactat    1020
cctgacaagg tgtttagaag ctccgtgctg cactctacac aggatctgtt tctgccattc    1080
tttagcaacg tgacctggtt ccacgccatc acgtgagcg gcaccaatgg cacaaagcgg    1140
ttcgacaatc ccgtgctgcc tttttaacgat ggcgtgtact cgcctctac cgagaagagc    1200
aacatcatca gaggctggat cttttggcacc acactggact ccaagacaca gtctctgctg    1260
atcgtgaaca atgccaccaa cgtggtcatc aaggtgtgcg agttccagtt ttgtaatgat    1320
cccttcctgg gcgtgtacta tcacaagaac aataagagct ggatggagtc cgagtttaga    1380
gtgtattcta gcgccaacaa ttgcacattt gagtacgtgt cccagccttt cctgatggac    1440
ctggagggca agcagggcaa tttcaagaac ctgagggagt cgtgtttaa gaatatcgat    1500
ggctacttca aaatctacag caagcacacc cccatcaacc tggtgcgcga cctgcctcag    1560
ggcttcagcg ccctggagcc cctggtggat ctgcctatcg gcatcaacat cacccggttt    1620
cagacactgc tggccctgca cagaagctac ctgacacccg cgactcctc tagcggatgg    1680
accgcaggag ctgccgccta ctatgtgggc tatctgcagc ccggaccctt cctgctgaag    1740
tacaacgaga atggcaccat cacagacgca gtggattgcg ccctggaccc cctgagcgag    1800
acaaagtgta cactgaagtc ctttaccgtg gagaagggca tctatcagac atccaatttc    1860
agggtgcagc caaccgagtc tatcgtgcgc tttcctaata tcacaaacct gtgcccattt    1920
ggcgaggtgt tcaacgcaac caggttcgcc agcgtgtacg catggaatag gaagcgcatc    1980
```

```
tctaactgcg tggccgacta tagcgtgctg tacaactccg cctctttcag caccttttaag    2040
tgctatggcg tgtcccccac aaagctgaat gacctgtgct ttaccaacgt gtacgccgat    2100
tctttcgtga tcagggggcga cgaggtgcgc cagatcgcac ctggacagac aggcaagatc    2160
gccgactaca attataagct gccagacgat ttcaccggct gcgtgatcgc ctggaacagc    2220
aacaatctgg attccaaggt cggcggcaac tacaattatc tgtaccggct gtttagaaag    2280
agcaatctga agcccttcga gagggacatc tctacagaaa tctaccaggc cggcagcacc    2340
ccttgcaatg gcgtggaggg ctttaactgt tatttcccac tgcagtccta cggcttccag    2400
cccacaaacg gcgtgggcta tcagccttac cgcgtggtgg tgctgagctt tgagctgctg    2460
cacgcaccag caacagtgtg cggacccaag aagtccacca atctggtgaa gaacaagtgc    2520
gtgaacttca acttcaacgg cctgaccggc acaggcgtgc tgaccgagtc caacaagaag    2580
ttcctgccat tcagcagtt cggcagggac atcgcagata ccacagacgc cgtgcgcgac    2640
ccacagaccc tggagatcct ggacatcaca ccctgctctt tcggcggcgt gagcgtgatc    2700
acaccaggca ccaatacaag caaccaggtg gccgtgctgt atcaggacgt gaattgtacc    2760
gaggtgcctg tggccatcca cgccgatcag ctgacccca catggcgggt gtacagcacc    2820
ggctccaacg tgttccagac aagagccgga tgcctgatcg gagcagagca cgtgaacaat    2880
tcctatgagt gcgacatccc aatcggcgcc ggcatctgtg cctcttacca gacccagaca    2940
aactctccca gaagagcccg gagcgtggcc tcccagtcta tcatcgccta ccatgtcc      3000
ctgggcgccg agaacagcgt ggcctactct aacaatagca tcgccatccc aaccaacttc    3060
acaatctctg tgaccacaga gatcctgccc gtgtccatga ccaagacatc tgtggactgc    3120
acaatgtata tctgtggcga ttctaccgag tgcagcaacc tgctgctgca gtacggcagc    3180
ttttgtaccc agctgaatag agccctgaca ggcatcgccg tggagcagga taagaacaca    3240
caggaggtgt tcgcccaggt gaagcaaatc tacaagaccc cccctatcaa ggactttggc    3300
ggcttcaatt tttcccagat cctgcctgat ccatccaagc cttctaagcg gagctttatc    3360
gaggacctgc tgttcaacaa ggtgaccctg gccgatgccg gcttcatcaa gcagtatggc    3420
gattgcctgg gcgacatcgc agcccgggac ctgatctgcg cccagaagtt taatggcctg    3480
accgtgctgc caccccctgct gacagatgag atgatcgcac agtacacaag cgccctgctg    3540
gccggcacca tcatccggg atggaccttc ggcgcaggag ccgccctgca gatccccttt    3600
gccatgcaga tggcctatag gttcaacggc atcggcgtga cccagaatgt gctgtacgag    3660
aaccagaagc tgatcgccaa tcagtttaac tccgccatcg gcaagatcca ggacagcctg    3720
tcctctacag cctccgccct gggcaagctg caggatgtgg tgaatcagaa cgcccaggcc    3780
ctgaataccc tggtgaagca gctgagcagc aacttcggcg ccatctctag cgtgctgaat    3840
gacatcctga gccggctgga caaggtggag gcagaggtgc agatcgaccg gctgatcaca    3900
ggcagactgc agtctctgca gacctatgtg acacagcagc tgatcagggc agcagagatc    3960
agggccagcg ccaatctggc agcaaccaag atgtccgagt gcgtgctggg ccagtctaag    4020
agagtggact tttgtggcaa gggctatcac ctgatgtcct tccctcagtc tgccccacac    4080
ggcgtggtgt tctgcacgt gacctacgtg cccgcccagg agaagaactt caccacagcc    4140
cctgccatct gccacgatgg caaggcccac tttccaaggg agggcgtgtt cgtgtccaac    4200
ggcacccact ggtttgtgac acagcgcaat ttctacgagc cccagatcat caccacagac    4260
aataccttcg tgagcggcaa ctgtgacgtg gtcatcggca tcgtgaacaa taccgtgtat    4320
gatccactgc agcccgagct ggacagcttt aaggaggagc tggataagta cttcaagaat    4380
```

```
cacacctccc ctgacgtgga tctgggcgac atcagcggca tcaatgcctc cgtggtgaac    4440
atccagaagg agatcgaccg cctgaacgag gtggccaaga atctgaacga gagcctgatc    4500
gatctgcagg agctgggcaa gtatgagcag tacatcaagt ggccctggta catctggctg    4560
ggcttcatcg ccggcctgat cgccatcgtg atggtgacca tcatgctgtg ctgtatgaca    4620
tcctgctgtt cttgcctgaa gggctgctgt agctgtggct cctgctgtaa gtttgatgaa    4680
gatgatagtg aacccgtgct gaaaggcgtg aagctgcatt acacctgagg atccactagt    4740
ccagtgtggt ggaattctgc agatatccag cacagtggcg gccgctcgag tctagagggc    4800
ccgtttaaac ccgctgatca gcctcgactg tgccttctag ttgccagcca tctgttgttt    4860
gcccctcccc cgtgccttcc ttgaccctgg aaggtgccac tcccactgtc ctttcctaat    4920
aaaatgagga aattgcatcg cattgtctga gtaggtgtca ttctattctg ggggtgggg    4980 tggggcagga cagcaagggg gaggattggg aagacaatag caggcatgct ggggatgcgg    5040
tgggctctat ggcttctgag gcggaaagaa ccagctgggg ctctagggg tatccccacg    5100 cgccctgtag cggcgcatta agcgcggcgg gtgtggtggt tacgcgcagc gtgaccgcta    5160
cacttgccag cgccctagcg cccgctcctt tcgctttctt cccttccttt ctcgccacgt    5220
tcgccggctt tccccgtcaa gctctaaatc ggggctccc tttagggttc cgatttagtg    5280
ctttacggca cctcgacccc aaaaaacttg attagggtga tggttcacgt agtgggccat    5340
cgccctgata gacggttttt cgccctttga cgttggagtc cacgttcttt aatagtggac    5400
tcttgttcca aactgaaca acactcaacc ctatctcggt ctattctttt gatttataag    5460
ggattttgcc gatttcggcc tattggttaa aaaatgagct gatttaacaa aaatttaacg    5520
cgaattaatt ctgtggaatg tgtgtcagtt agggtgtgga aagtccccag gctccccagc    5580
aggcagaagt atgcaaagca tgcatctcaa ttagtcagca accaggtgtg gaaagtcccc    5640
aggctcccca gcaggcagaa gtatgcaaag catgcatctc aattagtcag caaccatagt    5700
cccgccccta actccgccca tcccgcccct aactccgccc agttccgccc attctccgcc    5760
ccatggctga ctaattttt ttatttatgc agaggccgag gccgcctctg cctctgagct    5820
attccagaag tagtgaggag gcttttttgg aggcctaggc ttttgcaaaa agctcccggg    5880
agcttgtata tccattttcg gatctgatca agagacagga tgaggatcgt ttcgcatgat    5940
tgaacaagat ggattgcacg caggttctcc ggccgcttgg gtggagaggc tattcggcta    6000
tgactgggca caacagacaa tcggctgctc tgatgccgcc gtgttccggc tgtcagcgca    6060
ggggcgcccg gttcttttg tcaagaccga cctgtccggt gccctgaatg aactgcagga    6120
cgaggcagcg cggctatcgt ggctggccac gacgggcgtt ccttgcgcag ctgtgctcga    6180
cgttgtcact gaagcgggaa gggactggct gctattgggc gaagtgccgg ggcaggatct    6240
cctgtcatct caccttgctc ctgccgagaa agtatccatc atggctgatg caatgcggcg    6300
gctgcatacg cttgatccgg ctacctgccc attcgaccac caagcgaaac atcgcatcga    6360
gcgagcacgt actcggatgg aagccggtct tgtcgatcag gatgatctgg acgaagagca    6420
tcaggggctc gcgccagccg aactgttcgc caggctcaag gcgcgcatgc ccgacggcga    6480
ggatctcgtc gtgacccatg gcgatgcctg cttgccgaat atcatggtgg aaaatggccg    6540
cttttctgga ttcatcgact gtggccggct gggtgtggcg gaccgctatc aggacatagc    6600
gttggctacc cgtgatattg ctgaagagct tggcggcgaa tgggctgacc gcttcctcgt    6660
gctttacggt atcgccgctc ccgattcgca gcgcatcgcc ttctatcgcc ttcttgacga    6720
```

-continued

```
gttcttctga gcgggactct ggggttcgaa atgaccgacc aagcgacgcc caacctgcca      6780
tcacgagatt tcgattccac cgccgccttc tatgaaaggt tgggcttcgg aatcgttttc      6840
cgggacgccg gctggatgat cctccagcgc ggggatctca tgctggagtt cttcgcccac      6900
cccaacttgt ttattgcagc ttataatggt tacaaataaa gcaatagcat cacaaatttc      6960
acaaataaag cattttttc actgcattct agttgtggtt tgtccaaact catcaatgta      7020
tcttatcatg tctgtatacc gtcgacctct agctagagct tggcgtaatc atggtcatag      7080
ctgtttcctg tgtgaaattg ttatccgctc acaattccac acaacatacg agccggaagc      7140
ataaagtgta aagcctgggg tgcctaatga gtgagctaac tcacattaat tgcgttgcgc      7200
tcactgcccg ctttccagtc gggaaacctg tcgtgccagc tgcattaatg aatcggccaa      7260
cgcgcgggga gaggcggttt gcgtattggg cgctcttccg cttcctcgct cactgactcg      7320
ctgcgctcgg tcgttcggct gcggcgagcg gtatcagctc actcaaaggc ggtaatacgg      7380
ttatccacag aatcagggga taacgcagga agaacatgt gagcaaaagg ccagcaaaag       7440
gccaggaacc gtaaaaaggc cgcgttgctg cgttttttcc ataggctccg ccccctgac      7500 gagcatcaca aaaatcgacg ctcaagtcag aggtggcgaa acccgacagg actataaaga      7560
taccaggcgt ttccccctgg aagctccctc gtgcgctctc ctgttccgac cctgccgctt      7620
accggatacc tgtccgcctt tctcccttcg ggaagcgtgg cgctttctca gctcacgc       7680 tgtaggtatc tcagttcggt gtaggtcgtt cgctccaagc tgggctgtgt gcacgaaccc      7740
cccgttcagc ccgaccgctg cgccttatcc ggtaactatc gtcttgagtc aacccggta      7800 agacacgact tatcgccact ggcagcagcc actggtaaca ggattagcag agcgaggtat      7860
gtaggcggtg ctacagagtt cttgaagtgg tggcctaact acggctacac tagaagaaca      7920
gtatttggta tctgcgctct gctgaagcca gttaccttcg gaaaaagagt tggtagctct      7980
tgatccggca aacaaaccac cgctggtagc ggtggttttt ttgtttgcaa gcagcagatt      8040
acgcgcagaa aaaaggatc tcaagaagat cctttgatct tttctacggg gtctgacgct      8100
cagtggaacg aaaactcacg ttaagggatt ttggtcatga gattatcaaa aaggatcttc      8160
acctagatcc ttttaaatta aaatgaagt tttaaatcaa tctaaagtat atatgagtaa      8220
acttggtctg acagttacca atgcttaatc agtgaggcac ctatctcagc gatctgtcta      8280
tttcgttcat ccatagttgc ctgactcccc gtcgtgtaga taactacgat acgggagggc      8340
ttaccatctg gccccagtgc tgcaatgata ccgcgagacc cacgctcacc ggctccagat      8400
ttatcagcaa taaaccagcc agccggaagg gccgagcgca gaagtggtcc tgcaacttta      8460
tccgcctcca tccagtctat taattgttgc cgggaagcta gagtaagtag ttcgccagtt      8520
aatagtttgc gcaacgttgt tgccattgct acaggcatcg tggtgtcacg ctcgtcgttt      8580
ggtatggctt cattcagctc cggttcccaa cgatcaaggc gagttacatg atccccatg       8640 ttgtgcaaaa aagcggttag ctccttcggt cctccgatcg ttgtcagaag taagttggcc      8700
gcagtgttat cactcatggt tatggcagca ctgcataatt ctcttactgt catgccatcc      8760
gtaagatgct tttctgtgac tggtgagtac tcaaccaagt cattctgaga atagtgtatg      8820
cggcgaccga gttgctcttg cccggcgtca atacggata ataccgcgcc acatagcaga      8880
actttaaaag tgctcatcat tggaaaacgt tcttcgggc gaaaactctc aaggatctta      8940
ccgctgttga tccagttc gatgtaaccc actcgtgcac ccaactgatc ttcagcatct      9000 tttacttca ccagcgttc tgggtgagca aaaacaggaa ggcaaaatgc cgcaaaaaag       9060
ggaataaggg cgacacggaa atgttgaata ctcatactct tcctttttca atattattga      9120
```

```
agcatttatc agggttattg tctcatgagc ggatacatat ttgaatgtat ttagaaaaat    9180
aaacaaatag gggttccgcg cacatttccc cgaaaagtgc cacctgacgt c             9231

<210> SEQ ID NO 3
<211> LENGTH: 2076
<212> TYPE: DNA
<213> ORGANISM: Artificial Sequence
<220> FEATURE:
<223> OTHER INFORMATION: Gene insert: S1.opt

<400> SEQUENCE: 3
gctagcgcca ccatgtttgt ctttctggtc ctgctgcctc tggtgtcatc tcagtgcgtg      60
aacctgacta ctagaactca gctgcccct gcttatacta attccttcac ccggggcgtg     120
tactatcctg acaaggtgtt tagaagctcc gtgctgcact ctacacagga tctgtttctg     180
ccattcttta gcaacgtgac ctggttccac gccatccacg tgagcggcac caatggcaca     240
aagcggttcg acaatcccgt gctgcctttt aacgatggcg tgtacttcgc ctctaccgag     300
aagagcaaca tcatcagagg ctggatcttt ggcaccacac tggactccaa gacacagtct     360
ctgctgatcg tgaacaatgc caccaacgtg gtcatcaagg tgtgcgagtt ccagttttgt     420
aatgatccct cctgggcgt gtactatcac aagaacaata gagctggat ggagtccgag      480 tttagagtgt attctagcgc caacaattgc acatttgagt acgtgcccca gcctttcctg     540
atggacctgg agggcaagca gggcaatttc aagaacctga gggagttcgt gtttaagaat     600
atcgatggct acttcaaaat ctacagcaag cacaccccca tcaacctggt gcgcgacctg     660
cctcagggct tcagcgccct ggagcccctg gtggatctgc ctatcggcat caacatcacc     720
cggtttcaga cactgctggc cctgcacaga agctacctga cacccggcga ctcctctagc     780
ggatggaccg caggagctgc cgcctactat gtgggctatc tgcagccccg gaccttcctg     840
ctgaagtaca cgagaatgg caccatcaca gacgcagtgg attgcgccct ggacccctg       900 agcgagacaa agtgtacact gaagtccttt accgtggaga agggcatcta tcagacatcc     960
aatttcaggg tgcagccaac cgagtctatc gtgcgctttc ctaatatcac aaacctgtgc    1020
ccatttggcg aggtgttcaa cgcaaccagg ttcgccagcg tgtacgcatg gaataggaag    1080
cgcatctcta actgcgtggc cgactatagc gtgctgtaca actccgcctc tttcagcacc    1140
tttaagtgct atggcgtgtc ccccacaaag ctgaatgacc tgtgctttac aacgtgtac     1200 gccgattctt tcgtgatcag gggcgacgag gtgcgccaga tcgcacctgg acagacaggc    1260
aagatcgccg actacaatta taagctgcca gacgatttca ccggctgcgt gatcgcctgg    1320
aacagcaaca atctggattc caaggtcggc ggcaactaca attatctgta ccggctgttt    1380
agaaagagca tctgaagcc cttcgagagg gacatctcta cagaaatcta ccaggccggc    1440
agcacccctt gcaatggcgt ggagggcttt aactgttatt cccactgca gtcctacggc    1500 ttccagccca aaacggcgt gggctatcag ccttaccgcg tggtggtgct gagctttgag    1560
ctgctgcacg caccagcaac agtgtgcgga cccaagaagt ccaccaatct ggtgaagaac    1620
aagtgcgtga acttcaactt caacggcctg accggcacag gcgtgctgac cgagtccaac    1680
aagaagttcc tgccatttca gcagttcggc agggacatcg cagataccac agacgccgtg    1740
cgcgacccac agaccctgga gatcctggac atcacaccct gctctttcgg cggcgtgagc    1800
gtgatcacac caggcaccaa tacaagcaac caggtggccg tgctgtatca ggacgtgaat    1860
tgtaccgagg tgcctgtggc catccacgcc gatcagctga ccccaacatg gcgggtgtac    1920
```

-continued

| | |
|---|---|
| agcaccggct ccaacgtgtt ccagacaaga gccggatgcc tgatcggagc agagcacgtg | 1980 |
| aacaattcct atgagtgcga catcccaatc ggcgccggca tctgtgcctc ttaccagacc | 2040 |
| cagacaaact ctcccagaag agcccggtga ggatcc | 2076 |

<210> SEQ ID NO 4
<211> LENGTH: 7467
<212> TYPE: DNA
<213> ORGANISM: Artificial Sequence
<220> FEATURE:
<223> OTHER INFORMATION: S1.opt pcDNA 3.1(+) construct

<400> SEQUENCE: 4

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gccaccatgt ttgtctttct ggtcctgctg cctctggtgt catctcagtg cgtgaacctg | 960 |
| actactagaa ctcagctgcc ccctgcttat actaattcct tcacccgggg cgtgtactat | 1020 |
| cctgacaagg tgtttagaag ctccgtgctg cactctacac aggatctgtt tctgccattc | 1080 |
| tttagcaacg tgacctggtt ccacgccatc acgtgagcg gcaccaatgg cacaaagcgg | 1140 |
| ttcgacaatc ccgtgctgcc ttttaacgat ggcgtgtact tcgcctctac cgagaagagc | 1200 |
| aacatcatca gaggctggat cttttggcacc acactggact ccaagacaca gtctctgctg | 1260 |
| atcgtgaaca atgccaccaa cgtggtcatc aaggtgtgcg agttccagtt tgtaatgat | 1320 |
| cccttcctgg gcgtgtacta tcacaagaac aataagagct ggatggagtc cgagtttaga | 1380 |
| gtgtattcta gcgccaacaa ttgcacattt gagtacgtgt cccagccttt cctgatggac | 1440 |
| ctggagggca gcagggcaa tttcaagaac ctgagggagt tcgtgtttaa gaatatcgat | 1500 |
| ggctacttca aaatctacag caagcacacc cccatcaacc tggtgcgcga cctgcctcag | 1560 |
| ggcttcagcg ccctggagcc cctggtggat ctgcctatcg gcatcaacat cacccggttt | 1620 |
| cagacactgc tggccctgca cagaagctac ctgacacccg cgactcctc tagcggatgg | 1680 |
| accgcaggag ctgccgccta ctatgtgggc tatctgcagc ccggaccttt cctgctgaag | 1740 |
| tacaacgaga atggcaccat cacagacgca gtggattgcg ccctggaccc cctgagcgag | 1800 |
| acaaagtgta cactgaagtc ctttaccgtg gagaagggca tctatcagac atccaatttc | 1860 |
| agggtgcagc caaccgagtc tatcgtgcgc tttcctaata tcacaaacct gtgcccattt | 1920 |

-continued

```
ggcgaggtgt tcaacgcaac caggttcgcc agcgtgtacg catgaaatag gaagcgcatc    1980
tctaactgcg tggccgacta tagcgtgctg tacaactccg cctctttcag cacctttaag    2040
tgctatggcg tgtcccccac aaagctgaat gacctgtgct ttaccaacgt gtacgccgat    2100
tctttcgtga tcaggggcga cgaggtgcgc cagatcgcac ctggacagac aggcaagatc    2160
gccgactaca attataagct gccagacgat ttcaccggct gcgtgatcgc ctggaacagc    2220
aacaatctgg attccaaggt cggcggcaac tacaattatc tgtaccggct gtttagaaag    2280
agcaatctga agcccttcga gagggacatc tctacagaaa tctaccaggc cggcagcacc    2340
ccttgcaatg gcgtggaggg ctttaactgt tatttcccac tgcagtccta cggcttccag    2400
cccacaaacg gcgtgggcta tcagccttac cgcgtggtgg tgctgagctt tgagctgctg    2460
cacgcaccag caacagtgtg cggacccaag aagtccacca atctggtgaa gaacaagtgc    2520
gtgaacttca acttcaacgg cctgaccggc acaggcgtgc tgaccgagtc caacaagaag    2580
ttcctgccat tcagcagtt cggcaggac atcgcagata ccacagacgc cgtgcgcgac    2640
ccacagaccc tggagatcct ggacatcaca ccctgctctt tcggcggcgt gagcgtgatc    2700
acaccaggca ccaatacaag caaccaggtg gccgtgctgt atcaggacgt gaattgtacc    2760
gaggtgcctg tggccatcca cgccgatcag ctgacccaa catggcgggt gtacagcacc    2820
ggctccaacg tgttccagac aagagccgga tgcctgatcg gagcagagca cgtgaacaat    2880
tcctatgagt gcgacatccc aatcggcgcc ggcatctgtg cctcttacca gacccagaca    2940
aactctccca gaagagcccg gtgaggatcc actagtccag tgtggtggaa ttctgcagat    3000
atccagcaca gtggcggccg ctcgagtcta gagggcccgt ttaaacccgc tgatcagcct    3060
cgactgtgcc ttctagttgc cagccatctg ttgtttgccc ctcccccgtg ccttccttga    3120
ccctggaagg tgccactccc actgtccttt cctaataaaa tgaggaaatt gcatcgcatt    3180
gtctgagtag tgtcattct attctggggg gtggggtggg gcaggacagc aaggggagg    3240 attgggaaga caatagcagg catgctgggg atgcggtggg ctctatggct tctgaggcgg    3300
aaagaaccag ctggggctct aggggggtatc cccacgcgcc ctgtagcggc gcattaagcg    3360
cggcgggtgt ggtggttacg cgcagcgtga ccgctacact tgccagcgcc ctagcgcccg    3420
ctcctttcgc tttcttccct tcctttctcg ccacgttcgc cggctttccc cgtcaagctc    3480
taaatcgggg gctcccttta gggttccgat ttagtgcttt acggcacctc gaccccaaaa    3540
aacttgatta gggtgatggt tcacgtagtg ggccatcgcc ctgatagacg gttttcgcc    3600 ctttgacgtt ggagtccacg ttctttaata gtggactctt gttccaaact ggaacaacac    3660
tcaaccctat ctcggtctat tcttttgatt tataagggat tttgccgatt tcggcctatt    3720
ggttaaaaaa tgagctgatt taacaaaaat ttaacgcgaa ttaattctgt ggaatgtgtg    3780
tcagttaggg tgtggaaagt ccccaggctc cccagcaggc agaagtatgc aaagcatgca    3840
tctcaattag tcagcaacca ggtgtggaaa gtccccaggc tccccagcag gcagaagtat    3900
gcaaagcatg catctcaatt agtcagcaac catagtcccg cccctaactc cgcccatccc    3960
gcccctaact ccgcccagtt ccgcccattc tccgccccat ggctgactaa ttttttttat    4020
ttatgcagag gccgaggccg cctctgcctc tgagctattc cagaagtagt gaggaggctt    4080
ttttggaggc ctaggctttt gcaaaaagct cccgggagct gtatatcca ttttcggatc    4140 tgatcaagag acaggatgag gatcgtttcg catgattgaa caagatggat tgcacgcagg    4200
ttctccggcc gcttgggtgg agaggctatt cggctatgac tgggcacaac agacaatcgg    4260
```

-continued

```
ctgctctgat gccgccgtgt tccggctgtc agcgcagggg cgcccggttc ttttgtcaa     4320 gaccgacctg tccggtgccc tgaatgaact gcaggacgag gcagcgcggc tatcgtggct     4380
ggccacgacg ggcgttcctt gcgcagctgt gctcgacgtt gtcactgaag cgggaaggga     4440
ctggctgcta ttgggcgaag tgccggggca ggatctcctg tcatctcacc ttgctcctgc     4500
cgagaaagta tccatcatgg ctgatgcaat gcggcggctg catacgcttg atccggctac     4560
ctgcccattc gaccaccaag cgaaacatcg catcgagcga gcacgtactc ggatggaagc     4620
cggtcttgtc gatcaggatg atctggacga agagcatcag gggctcgcgc cagccgaact     4680
gttcgccagg ctcaaggcgc gcatgcccga cggcgaggat ctcgtcgtga cccatggcga     4740
tgcctgcttg ccgaatatca tggtggaaaa tggccgcttt tctggattca tcgactgtgg     4800
ccggctgggt gtggcggacc gctatcagga catagcgttg ctacccgtg atattgctga     4860 agagcttggc ggcgaatggg ctgaccgctt cctcgtgctt tacggtatcg ccgctcccga     4920
ttcgcagcgc atcgccttct atcgccttct tgacgagttc ttctgagcgg gactctgggg     4980
ttcgaaatga ccgaccaagc gacgcccaac ctgccatcac gagatttcga ttccaccgcc     5040
gccttctatg aaaggttggg cttcggaatc gttttccggg acgccggctg gatgatcctc     5100
cagcgcgggg atctcatgct ggagttcttc gcccacccca acttgtttat tgcagcttat     5160
aatggttaca ataaagcaa tagcatcaca aatttcacaa ataaagcatt ttttcactg     5220 cattctagtt gtggtttgtc caaactcatc aatgtatctt atcatgtctg tataccgtcg     5280
acctctagct agagcttggc gtaatcatgg tcatagctgt ttcctgtgtg aaattgttat     5340
ccgctcacaa ttccacacaa catacgagcc ggaagcataa agtgtaaagc ctggggtgcc     5400
taatgagtga gctaactcac attaattgcg ttgcgctcac tgcccgcttt ccagtcggga     5460
aacctgtcgt gccagctgca ttaatgaatc ggccaacgcg cggggagagg cggtttgcgt     5520
attgggcgct cttccgcttc ctcgctcact gactcgctgc gctcggtcgt tcggctgcgg     5580
cgagcggtat cagctcactc aaaggcggta atacggttat ccacagaatc aggggataac     5640
gcaggaaaga acatgtgagc aaaaggccag caaaaggcca ggaaccgtaa aaaggccgcg     5700
ttgctggcgt ttttccatag gctccgcccc cctgacgagc atcacaaaaa tcgacgctca     5760
agtcagaggt ggcgaaaccc gacaggacta taaagatacc aggcgtttcc ccctggaagc     5820
tccctcgtgc gctctcctgt tccgaccctg ccgcttaccg gatacctgtc cgcctttctc     5880
ccttcgggaa gcgtggcgct ttctcatagc tcacgctgta ggtatctcag ttcggtgtag     5940
gtcgttcgct ccaagctggg ctgtgtgcac gaaccccccg ttcagcccga ccgctgcgcc     6000
ttatccggta actatcgtct tgagtccaac ccggtaagac acgacttatc gccactggca     6060
gcagccactg gtaacaggat tagcagagcg aggtatgtag gcggtgctac agagttcttg     6120
aagtggtggc ctaactacgg ctacactaga agaacagtat ttggtatctg cgctctgctg     6180
aagccagtta ccttcggaaa aagagttggt agctcttgat ccggcaaaca aaccaccgct     6240
ggtagcggtg gtttttttgt ttgcaagcag cagattacgc gcagaaaaaa aggatctcaa     6300
gaagatcctt tgatcttttc tacggggtct gacgctcagt ggaacgaaaa ctcacgttaa     6360
gggattttgg tcatgagatt atcaaaaagg atcttcacct agatcctttt aaattaaaaa     6420
tgaagtttta aatcaatcta agtatatat gagtaaactt ggtctgacag ttaccaatgc     6480
ttaatcagtg aggcacctat ctcagcgatc tgtctatttc gttcatccat agttgcctga     6540
ctccccgtcg tgtagataac tacgatacgg gagggcttac catctggccc cagtgctgca     6600
atgataccgc gagacccacg ctcaccggct ccagatttat cagcaataaa ccagccagcc     6660
```

-continued

```
ggaagggccg agcgcagaag tggtcctgca actttatccg cctccatcca gtctattaat    6720
tgttgccggg aagctagagt aagtagttcg ccagttaata gtttgcgcaa cgttgttgcc    6780
attgctacag gcatcgtggt gtcacgctcg tcgtttggta tggcttcatt cagctccggt    6840
tcccaacgat caaggcgagt tacatgatcc cccatgttgt gcaaaaaagc ggttagctcc    6900
ttcggtcctc cgatcgttgt cagaagtaag ttggccgcag tgttatcact catggttatg    6960
gcagcactgc ataattctct tactgtcatg ccatccgtaa gatgcttttc tgtgactggt    7020
gagtactcaa ccaagtcatt ctgagaatag tgtatgcggc gaccgagttg ctcttgcccg    7080
gcgtcaatac gggataatac cgcgccacat agcagaactt taaaagtgct catcattgga    7140
aaacgttctt cggggcgaaa actctcaagg atcttaccgc tgttgagatc cagttcgatg    7200
taacccactc gtgcacccaa ctgatcttca gcatcttta ctttcaccag cgtttctggg    7260
tgagcaaaaa caggaaggca aaatgccgca aaaaagggaa taagggcgac acggaaatgt    7320
tgaatactca tactcttcct ttttcaatat tattgaagca tttatcaggg ttattgtctc    7380
atgagcggat acatatttga atgtatttag aaaaataaac aaataggggt tccgcgcaca    7440 tttcccgaa aagtgccacc tgacgtc                                         7467
```

<210> SEQ ID NO 5
<211> LENGTH: 10
<212> TYPE: DNA
<213> ORGANISM: Artificial Sequence
<220> FEATURE:
<223> OTHER INFORMATION: Kozac motif vetebrates

<400> SEQUENCE: 5

```
gccrccatgg                                                                10
```

<210> SEQ ID NO 6
<211> LENGTH: 3822
<212> TYPE: DNA
<213> ORGANISM: SARS COV 2 isolate Wuhan Hu 1
<220> FEATURE:
<221> NAME/KEY: CDS
<222> LOCATION: (1)..(3822)

<400> SEQUENCE: 6

```
atg ttt gtt ttt ctt gtt tta ttg cca cta gtc tct agt cag tgt gtt       48
Met Phe Val Phe Leu Val Leu Leu Pro Leu Val Ser Ser Gln Cys Val
1               5                   10                  15 aat ctt aca acc aga act caa tta ccc cct gca tac act aat tct ttc       96
Asn Leu Thr Thr Arg Thr Gln Leu Pro Pro Ala Tyr Thr Asn Ser Phe
            20                  25                  30 aca cgt ggt gtt tat tac cct gac aaa gtt ttc aga tcc tca gtt tta      144
Thr Arg Gly Val Tyr Tyr Pro Asp Lys Val Phe Arg Ser Ser Val Leu
        35                  40                  45 cat tca act cag gac ttg ttc tta cct ttc ttt tcc aat gtt act tgg      192
His Ser Thr Gln Asp Leu Phe Leu Pro Phe Phe Ser Asn Val Thr Trp
    50                  55                  60 ttc cat gct ata cat gtc tct ggg acc aat ggt act aag agg ttt gat      240
Phe His Ala Ile His Val Ser Gly Thr Asn Gly Thr Lys Arg Phe Asp
65                  70                  75                  80 aac cct gtc cta cca ttt aat gat ggt gtt tat ttt gct tcc act gag      288
Asn Pro Val Leu Pro Phe Asn Asp Gly Val Tyr Phe Ala Ser Thr Glu
                85                  90                  95 aag tct aac ata ata aga ggc tgg att ttt ggt act act tta gat tcg      336
Lys Ser Asn Ile Ile Arg Gly Trp Ile Phe Gly Thr Thr Leu Asp Ser
            100                 105                 110
```

```
                                           -continued aag acc cag tcc cta ctt att gtt aat aac gct act aat gtt gtt att        384
Lys Thr Gln Ser Leu Leu Ile Val Asn Asn Ala Thr Asn Val Val Ile
        115                 120                 125 aaa gtc tgt gaa ttt caa ttt tgt aat gat cca ttt ttg ggt gtt tat        432
Lys Val Cys Glu Phe Gln Phe Cys Asn Asp Pro Phe Leu Gly Val Tyr
130                 135                 140 tac cac aaa aac aac aaa agt tgg atg gaa agt gag ttc aga gtt tat        480
Tyr His Lys Asn Asn Lys Ser Trp Met Glu Ser Glu Phe Arg Val Tyr
145                 150                 155                 160 tct agt gcg aat aat tgc act ttt gaa tat gtc tct cag cct ttt ctt        528
Ser Ser Ala Asn Asn Cys Thr Phe Glu Tyr Val Ser Gln Pro Phe Leu
                165                 170                 175 atg gac ctt gaa gga aaa cag ggt aat ttc aaa aat ctt agg gaa ttt        576
Met Asp Leu Glu Gly Lys Gln Gly Asn Phe Lys Asn Leu Arg Glu Phe
            180                 185                 190 gtg ttt aag aat att gat ggt tat ttt aaa ata tat tct aag cac acg        624
Val Phe Lys Asn Ile Asp Gly Tyr Phe Lys Ile Tyr Ser Lys His Thr
        195                 200                 205 cct att aat tta gtg cgt gat ctc cct cag ggt ttt tcg gct tta gaa        672
Pro Ile Asn Leu Val Arg Asp Leu Pro Gln Gly Phe Ser Ala Leu Glu
210                 215                 220 cca ttg gta gat ttg cca ata ggt att aac atc act agg ttt caa act        720
Pro Leu Val Asp Leu Pro Ile Gly Ile Asn Ile Thr Arg Phe Gln Thr
225                 230                 235                 240 tta ctt gct tta cat aga agt tat ttg act cct ggt gat tct tct tca        768
Leu Leu Ala Leu His Arg Ser Tyr Leu Thr Pro Gly Asp Ser Ser Ser
                245                 250                 255 ggt tgg aca gct ggt gct gca gct tat tat gtg ggt tat ctt caa cct        816
Gly Trp Thr Ala Gly Ala Ala Ala Tyr Tyr Val Gly Tyr Leu Gln Pro
            260                 265                 270 agg act ttt cta tta aaa tat aat gaa aat gga acc att aca gat gct        864
Arg Thr Phe Leu Leu Lys Tyr Asn Glu Asn Gly Thr Ile Thr Asp Ala
        275                 280                 285 gta gac tgt gca ctt gac cct ctc tca gaa aca aag tgt acg ttg aaa        912
Val Asp Cys Ala Leu Asp Pro Leu Ser Glu Thr Lys Cys Thr Leu Lys
290                 295                 300 tcc ttc act gta gaa aaa gga atc tat caa act tct aac ttt aga gtc        960
Ser Phe Thr Val Glu Lys Gly Ile Tyr Gln Thr Ser Asn Phe Arg Val
305                 310                 315                 320 caa cca aca gaa tct att gtt aga ttt cct aat att aca aac ttg tgc        1008
Gln Pro Thr Glu Ser Ile Val Arg Phe Pro Asn Ile Thr Asn Leu Cys
                325                 330                 335 cct ttt ggt gaa gtt ttt aac gcc acc aga ttt gca tct gtt tat gct        1056
Pro Phe Gly Glu Val Phe Asn Ala Thr Arg Phe Ala Ser Val Tyr Ala
            340                 345                 350 tgg aac agg aag aga atc agc aac tgt gtt gct gat tat tct gtc cta        1104
Trp Asn Arg Lys Arg Ile Ser Asn Cys Val Ala Asp Tyr Ser Val Leu
        355                 360                 365 tat aat tcc gca tca ttt tcc act ttt aag tgt tat gga gtg tct cct        1152
Tyr Asn Ser Ala Ser Phe Ser Thr Phe Lys Cys Tyr Gly Val Ser Pro
370                 375                 380 act aaa tta aat gat ctc tgc ttt act aat gtc tat gca gat tca ttt        1200
Thr Lys Leu Asn Asp Leu Cys Phe Thr Asn Val Tyr Ala Asp Ser Phe
385                 390                 395                 400 gta att aga ggt gat gaa gtc aga caa atc gct cca ggg caa act gga        1248
Val Ile Arg Gly Asp Glu Val Arg Gln Ile Ala Pro Gly Gln Thr Gly
                405                 410                 415 aag att gct gat tat aat tat aaa tta cca gat gat ttt aca ggc tgc        1296
Lys Ile Ala Asp Tyr Asn Tyr Lys Leu Pro Asp Asp Phe Thr Gly Cys
```

```
                    420             425             430
gtt ata gct tgg aat tct aac aat ctt gat tct aag gtt ggt ggt aat    1344
Val Ile Ala Trp Asn Ser Asn Asn Leu Asp Ser Lys Val Gly Gly Asn
            435             440             445 tat aat tac ctg tat aga ttg ttt agg aag tct aat ctc aaa cct ttt    1392
Tyr Asn Tyr Leu Tyr Arg Leu Phe Arg Lys Ser Asn Leu Lys Pro Phe
450             455             460 gag aga gat att tca act gaa atc tat cag gcc ggt agc aca cct tgt    1440
Glu Arg Asp Ile Ser Thr Glu Ile Tyr Gln Ala Gly Ser Thr Pro Cys
465             470             475             480 aat ggt gtt gaa ggt ttt aat tgt tac ttt cct tta caa tca tat ggt    1488
Asn Gly Val Glu Gly Phe Asn Cys Tyr Phe Pro Leu Gln Ser Tyr Gly
            485             490             495 ttc caa ccc act aat ggt gtt ggt tac caa cca tac aga gta gta gta    1536
Phe Gln Pro Thr Asn Gly Val Gly Tyr Gln Pro Tyr Arg Val Val Val
                500             505             510 ctt tct ttt gaa ctt cta cat gca cca gca act gtt tgt gga cct aaa    1584
Leu Ser Phe Glu Leu Leu His Ala Pro Ala Thr Val Cys Gly Pro Lys
            515             520             525 aag tct act aat ttg gtt aaa aac aaa tgt gtc aat ttc aac ttc aat    1632
Lys Ser Thr Asn Leu Val Lys Asn Lys Cys Val Asn Phe Asn Phe Asn
530             535             540 ggt tta aca ggc aca ggt gtt ctt act gag tct aac aaa aag ttt ctg    1680
Gly Leu Thr Gly Thr Gly Val Leu Thr Glu Ser Asn Lys Lys Phe Leu
545             550             555             560 cct ttc caa caa ttt ggc aga gac att gct gac act act gat gct gtc    1728
Pro Phe Gln Gln Phe Gly Arg Asp Ile Ala Asp Thr Thr Asp Ala Val
            565             570             575 cgt gat cca cag aca ctt gag att ctt gac att aca cca tgt tct ttt    1776
Arg Asp Pro Gln Thr Leu Glu Ile Leu Asp Ile Thr Pro Cys Ser Phe
            580             585             590 ggt ggt gtc agt gtt ata aca cca gga aca aat act tct aac cag gtt    1824
Gly Gly Val Ser Val Ile Thr Pro Gly Thr Asn Thr Ser Asn Gln Val
            595             600             605 gct gtt ctt tat cag gat gtt aac tgc aca gaa gtc cct gtt gct att    1872
Ala Val Leu Tyr Gln Asp Val Asn Cys Thr Glu Val Pro Val Ala Ile
610             615             620 cat gca gat caa ctt act cct act tgg cgt gtt tat tct aca ggt tct    1920
His Ala Asp Gln Leu Thr Pro Thr Trp Arg Val Tyr Ser Thr Gly Ser
625             630             635             640 aat gtt ttt caa aca cgt gca ggc tgt tta ata ggg gct gaa cat gtc    1968
Asn Val Phe Gln Thr Arg Ala Gly Cys Leu Ile Gly Ala Glu His Val
            645             650             655 aac aac tca tat gag tgt gac ata ccc att ggt gca ggt ata tgc gct    2016
Asn Asn Ser Tyr Glu Cys Asp Ile Pro Ile Gly Ala Gly Ile Cys Ala
            660             665             670 agt tat cag act cag act aat tct cct cgg cgg gca cgt agt gta gct    2064
Ser Tyr Gln Thr Gln Thr Asn Ser Pro Arg Arg Ala Arg Ser Val Ala
            675             680             685 agt caa tcc atc att gcc tac act atg tca ctt ggt gca gaa aat tca    2112
Ser Gln Ser Ile Ile Ala Tyr Thr Met Ser Leu Gly Ala Glu Asn Ser
            690             695             700 gtt gct tac tct aat aac tct att gcc ata ccc aca aat ttt act att    2160
Val Ala Tyr Ser Asn Asn Ser Ile Ala Ile Pro Thr Asn Phe Thr Ile
705             710             715             720 agt gtt acc aca gaa att cta cca gtg tct atg acc aag aca tca gta    2208
Ser Val Thr Thr Glu Ile Leu Pro Val Ser Met Thr Lys Thr Ser Val
                725             730             735 gat tgt aca atg tac att tgt ggt gat tca act gaa tgc agc aat ctt    2256
```

```
                Asp Cys Thr Met Tyr Ile Cys Gly Asp Ser Thr Glu Cys Ser Asn Leu
                            740                 745                 750 ttg ttg caa tat ggc agt ttt tgt aca caa tta aac cgt gct tta act              2304
Leu Leu Gln Tyr Gly Ser Phe Cys Thr Gln Leu Asn Arg Ala Leu Thr
            755                 760                 765 gga ata gct gtt gaa caa gac aaa aac acc caa gaa gtt ttt gca caa              2352
Gly Ile Ala Val Glu Gln Asp Lys Asn Thr Gln Glu Val Phe Ala Gln
770                 775                 780 gtc aaa caa att tac aaa aca cca cca att aaa gat ttt ggt ggt ttt              2400
Val Lys Gln Ile Tyr Lys Thr Pro Pro Ile Lys Asp Phe Gly Gly Phe
785                 790                 795                 800 aat ttt tca caa ata tta cca gat cca tca aaa cca agc aag agg tca              2448
Asn Phe Ser Gln Ile Leu Pro Asp Pro Ser Lys Pro Ser Lys Arg Ser
                805                 810                 815 ttt att gaa gat cta ctt ttc aac aaa gtg aca ctt gca gat gct ggc              2496
Phe Ile Glu Asp Leu Leu Phe Asn Lys Val Thr Leu Ala Asp Ala Gly
            820                 825                 830 ttc atc aaa caa tat ggt gat tgc ctt ggt gat att gct gct aga gac              2544
Phe Ile Lys Gln Tyr Gly Asp Cys Leu Gly Asp Ile Ala Ala Arg Asp
        835                 840                 845 ctc att tgt gca caa aag ttt aac ggc ctt act gtt ttg cca cct ttg              2592
Leu Ile Cys Ala Gln Lys Phe Asn Gly Leu Thr Val Leu Pro Pro Leu
    850                 855                 860 ctc aca gat gaa atg att gct caa tac act tct gca ctg tta gcg ggt              2640
Leu Thr Asp Glu Met Ile Ala Gln Tyr Thr Ser Ala Leu Leu Ala Gly
865                 870                 875                 880 aca atc act tct ggt tgg acc ttt ggt gca ggt gct gca tta caa ata              2688
Thr Ile Thr Ser Gly Trp Thr Phe Gly Ala Gly Ala Ala Leu Gln Ile
                885                 890                 895 cca ttt gct atg caa atg gct tat agg ttt aat ggt att gga gtt aca              2736
Pro Phe Ala Met Gln Met Ala Tyr Arg Phe Asn Gly Ile Gly Val Thr
            900                 905                 910 cag aat gtt ctc tat gag aac caa aaa ttg att gcc aac caa ttt aat              2784
Gln Asn Val Leu Tyr Glu Asn Gln Lys Leu Ile Ala Asn Gln Phe Asn
        915                 920                 925 agt gct att ggc aaa att caa gac tca ctt tct tcc aca gca agt gca              2832
Ser Ala Ile Gly Lys Ile Gln Asp Ser Leu Ser Ser Thr Ala Ser Ala
    930                 935                 940 ctt gga aaa ctt caa gat gtg gtc aac caa aat gca caa gct tta aac              2880
Leu Gly Lys Leu Gln Asp Val Val Asn Gln Asn Ala Gln Ala Leu Asn
945                 950                 955                 960 acg ctt gtt aaa caa ctt agc tcc aat ttt ggt gca att tca agt gtt              2928
Thr Leu Val Lys Gln Leu Ser Ser Asn Phe Gly Ala Ile Ser Ser Val
                965                 970                 975 tta aat gat atc ctt tca cgt ctt gac aaa gtt gag gct gaa gtg caa              2976
Leu Asn Asp Ile Leu Ser Arg Leu Asp Lys Val Glu Ala Glu Val Gln
            980                 985                 990 att gat agg ttg atc aca ggc aga ctt caa agt ttg cag aca tat gtg              3024
Ile Asp Arg Leu Ile Thr Gly Arg Leu Gln Ser Leu Gln Thr Tyr Val
        995                 1000                1005 act caa caa tta att aga gct gca gaa atc aga gct tct gct aat              3069
Thr Gln Gln Leu Ile Arg Ala Ala Glu Ile Arg Ala Ser Ala Asn
    1010                1015                1020 ctt gct gct act aaa atg tca gag tgt gta ctt gga caa tca aaa              3114
Leu Ala Ala Thr Lys Met Ser Glu Cys Val Leu Gly Gln Ser Lys
    1025                1030                1035 aga gtt gat ttt tgt gga aag ggc tat cat ctt atg tcc ttc cct              3159
Arg Val Asp Phe Cys Gly Lys Gly Tyr His Leu Met Ser Phe Pro
    1040                1045                1050
```

| | | | | | | | | | | | | | | |
|---|---|---|---|---|---|---|---|---|---|---|---|---|---|---|
| cag | tca | gca | cct | cat | ggt | gta | gtc | ttc | ttg | cat | gtg | act | tat | gtc | 3204 |
| Gln | Ser | Ala | Pro | His | Gly | Val | Val | Phe | Leu | His | Val | Thr | Tyr | Val | |
| | 1055 | | | | 1060 | | | | | 1065 | | | | | |

| | | | | | | | | | | | | | | | |
|---|---|---|---|---|---|---|---|---|---|---|---|---|---|---|---|
| cct | gca | caa | gaa | aag | aac | ttc | aca | act | gct | cct | gcc | att | tgt | cat | 3249 |
| Pro | Ala | Gln | Glu | Lys | Asn | Phe | Thr | Thr | Ala | Pro | Ala | Ile | Cys | His | |
| 1070 | | | | | 1075 | | | | | 1080 | | | | | |

| | | | | | | | | | | | | | | | |
|---|---|---|---|---|---|---|---|---|---|---|---|---|---|---|---|
| gat | gga | aaa | gca | cac | ttt | cct | cgt | gaa | ggt | gtc | ttt | gtt | tca | aat | 3294 |
| Asp | Gly | Lys | Ala | His | Phe | Pro | Arg | Glu | Gly | Val | Phe | Val | Ser | Asn | |
| 1085 | | | | | 1090 | | | | | 1095 | | | | | |

| | | | | | | | | | | | | | | | |
|---|---|---|---|---|---|---|---|---|---|---|---|---|---|---|---|
| ggc | aca | cac | tgg | ttt | gta | aca | caa | agg | aat | ttt | tat | gaa | cca | caa | 3339 |
| Gly | Thr | His | Trp | Phe | Val | Thr | Gln | Arg | Asn | Phe | Tyr | Glu | Pro | Gln | |
| 1100 | | | | | 1105 | | | | | 1110 | | | | | |

| | | | | | | | | | | | | | | | |
|---|---|---|---|---|---|---|---|---|---|---|---|---|---|---|---|
| atc | att | act | aca | gac | aac | aca | ttt | gtg | tct | ggt | aac | tgt | gat | gtt | 3384 |
| Ile | Ile | Thr | Thr | Asp | Asn | Thr | Phe | Val | Ser | Gly | Asn | Cys | Asp | Val | |
| 1115 | | | | | 1120 | | | | | 1125 | | | | | |

| | | | | | | | | | | | | | | | |
|---|---|---|---|---|---|---|---|---|---|---|---|---|---|---|---|
| gta | ata | gga | att | gtc | aac | aac | aca | gtt | tat | gat | cct | ttg | caa | cct | 3429 |
| Val | Ile | Gly | Ile | Val | Asn | Asn | Thr | Val | Tyr | Asp | Pro | Leu | Gln | Pro | |
| 1130 | | | | | 1135 | | | | | 1140 | | | | | |

| | | | | | | | | | | | | | | | |
|---|---|---|---|---|---|---|---|---|---|---|---|---|---|---|---|
| gaa | tta | gac | tca | ttc | aag | gag | gag | tta | gat | aaa | tat | ttt | aag | aat | 3474 |
| Glu | Leu | Asp | Ser | Phe | Lys | Glu | Glu | Leu | Asp | Lys | Tyr | Phe | Lys | Asn | |
| 1145 | | | | | 1150 | | | | | 1155 | | | | | |

| | | | | | | | | | | | | | | | |
|---|---|---|---|---|---|---|---|---|---|---|---|---|---|---|---|
| cat | aca | tca | cca | gat | gtt | gat | tta | ggt | gac | atc | tct | ggc | att | aat | 3519 |
| His | Thr | Ser | Pro | Asp | Val | Asp | Leu | Gly | Asp | Ile | Ser | Gly | Ile | Asn | |
| 1160 | | | | | 1165 | | | | | 1170 | | | | | |

| | | | | | | | | | | | | | | | |
|---|---|---|---|---|---|---|---|---|---|---|---|---|---|---|---|
| gct | tca | gtt | gta | aac | att | caa | aaa | gaa | att | gac | cgc | ctc | aat | gag | 3564 |
| Ala | Ser | Val | Val | Asn | Ile | Gln | Lys | Glu | Ile | Asp | Arg | Leu | Asn | Glu | |
| 1175 | | | | | 1180 | | | | | 1185 | | | | | |

| | | | | | | | | | | | | | | | |
|---|---|---|---|---|---|---|---|---|---|---|---|---|---|---|---|
| gtt | gcc | aag | aat | tta | aat | gaa | tct | ctc | atc | gat | ctc | caa | gaa | ctt | 3609 |
| Val | Ala | Lys | Asn | Leu | Asn | Glu | Ser | Leu | Ile | Asp | Leu | Gln | Glu | Leu | |
| 1190 | | | | | 1195 | | | | | 1200 | | | | | |

| | | | | | | | | | | | | | | | |
|---|---|---|---|---|---|---|---|---|---|---|---|---|---|---|---|
| gga | aag | tat | gag | cag | tat | ata | aaa | tgg | cca | tgg | tac | att | tgg | cta | 3654 |
| Gly | Lys | Tyr | Glu | Gln | Tyr | Ile | Lys | Trp | Pro | Trp | Tyr | Ile | Trp | Leu | |
| 1205 | | | | | 1210 | | | | | 1215 | | | | | |

| | | | | | | | | | | | | | | | |
|---|---|---|---|---|---|---|---|---|---|---|---|---|---|---|---|
| ggt | ttt | ata | gct | ggc | ttg | att | gcc | ata | gta | atg | gtg | aca | att | atg | 3699 |
| Gly | Phe | Ile | Ala | Gly | Leu | Ile | Ala | Ile | Val | Met | Val | Thr | Ile | Met | |
| 1220 | | | | | 1225 | | | | | 1230 | | | | | |

| | | | | | | | | | | | | | | | |
|---|---|---|---|---|---|---|---|---|---|---|---|---|---|---|---|
| ctt | tgc | tgt | atg | acc | agt | tgc | tgt | agt | tgt | ctc | aag | ggc | tgt | tgt | 3744 |
| Leu | Cys | Cys | Met | Thr | Ser | Cys | Cys | Ser | Cys | Leu | Lys | Gly | Cys | Cys | |
| 1235 | | | | | 1240 | | | | | 1245 | | | | | |

| | | | | | | | | | | | | | | | |
|---|---|---|---|---|---|---|---|---|---|---|---|---|---|---|---|
| tct | tgt | gga | tcc | tgc | tgc | aaa | ttt | gat | gaa | gac | gac | tct | gag | cca | 3789 |
| Ser | Cys | Gly | Ser | Cys | Cys | Lys | Phe | Asp | Glu | Asp | Asp | Ser | Glu | Pro | |
| 1250 | | | | | 1255 | | | | | 1260 | | | | | |

| | | | | | | | | |
|---|---|---|---|---|---|---|---|---|
| gtg | ctc | aaa | gga | gtc | aaa | tta | cat | tac | aca | taa | 3822 |
| Val | Leu | Lys | Gly | Val | Lys | Leu | His | Tyr | Thr | | |
| 1265 | | | | | 1270 | | | | | | |

```
<210> SEQ ID NO 7
<211> LENGTH: 1273
<212> TYPE: PRT
<213> ORGANISM: SARS COV 2 isolate Wuhan Hu 1

<400> SEQUENCE: 7

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

```
Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480
```

```
Asn Gly Val Glu Gly Phe Asn Cys Tyr Phe Pro Leu Gln Ser Tyr Gly
            485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
            515                 520                 525
Lys Ser Thr Asn Leu Val Lys Asn Lys Cys Val Asn Phe Asn Phe Asn
            530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
            565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
            610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
            645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
            675                 680                 685
Ser Gln Ser Ile Ile Ala Tyr Thr Met Ser Leu Gly Ala Glu Asn Ser
            690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
            725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
            755                 760                 765
Gly Ile Ala Val Glu Gln Asp Lys Asn Thr Gln Glu Val Phe Ala Gln
            770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
            805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
            835                 840                 845
Leu Ile Cys Ala Gln Lys Phe Asn Gly Leu Thr Val Leu Pro Pro Leu
            850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
            885                 890                 895
Pro Phe Ala Met Gln Met Ala Tyr Arg Phe Asn Gly Ile Gly Val Thr
```

```
                900           905              910
Gln Asn Val Leu Tyr Glu Asn Gln Lys Leu Ile Ala Asn Gln Phe Asn
            915              920              925

Ser Ala Ile Gly Lys Ile Gln Asp Ser Leu Ser Ser Thr Ala Ser Ala
930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
                965              970              975

Leu Asn Asp Ile Leu Ser Arg Leu Asp Lys Val Glu Ala Glu Val Gln
            980              985              990

Ile Asp Arg Leu Ile Thr Gly Arg Leu Gln Ser Leu Gln Thr Tyr Val
            995              1000             1005

Thr Gln Gln Leu Ile Arg Ala Ala Glu Ile Arg Ala Ser Ala Asn
        1010             1015             1020

Leu Ala Ala Thr Lys Met Ser Glu Cys Val Leu Gly Gln Ser Lys
        1025             1030             1035

Arg Val Asp Phe Cys Gly Lys Gly Tyr His Leu Met Ser Phe Pro
        1040             1045             1050

Gln Ser Ala Pro His Gly Val Val Phe Leu His Val Thr Tyr Val
        1055             1060             1065

Pro Ala Gln Glu Lys Asn Phe Thr Thr Ala Pro Ala Ile Cys His
        1070             1075             1080

Asp Gly Lys Ala His Phe Pro Arg Glu Gly Val Phe Val Ser Asn
        1085             1090             1095

Gly Thr His Trp Phe Val Thr Gln Arg Asn Phe Tyr Glu Pro Gln
        1100             1105             1110

Ile Ile Thr Thr Asp Asn Thr Phe Val Ser Gly Asn Cys Asp Val
        1115             1120             1125

Val Ile Gly Ile Val Asn Asn Thr Val Tyr Asp Pro Leu Gln Pro
        1130             1135             1140

Glu Leu Asp Ser Phe Lys Glu Glu Leu Asp Lys Tyr Phe Lys Asn
        1145             1150             1155

His Thr Ser Pro Asp Val Asp Leu Gly Asp Ile Ser Gly Ile Asn
        1160             1165             1170

Ala Ser Val Val Asn Ile Gln Lys Glu Ile Asp Arg Leu Asn Glu
        1175             1180             1185

Val Ala Lys Asn Leu Asn Glu Ser Leu Ile Asp Leu Gln Glu Leu
        1190             1195             1200

Gly Lys Tyr Glu Gln Tyr Ile Lys Trp Pro Trp Tyr Ile Trp Leu
        1205             1210             1215

Gly Phe Ile Ala Gly Leu Ile Ala Ile Val Met Val Thr Ile Met
        1220             1225             1230

Leu Cys Cys Met Thr Ser Cys Cys Ser Cys Leu Lys Gly Cys Cys
        1235             1240             1245

Ser Cys Gly Ser Cys Cys Lys Phe Asp Glu Asp Asp Ser Glu Pro
        1250             1255             1260

Val Leu Lys Gly Val Lys Leu His Tyr Thr
        1265             1270
```

SYNTHETIC PDNA VACCINES AGAINST COVID-19

REFERENCE TO A SEQUENCE LISTING

In accordance with 37 CFR § 1.52(e)(5), the present specification makes reference to a Sequence Listing submitted electronically as a .txt file named "535267US_ST25.txt". The .txt file was generated on Apr. 30, 2021, and is 60,168 bytes in size. The entire contents of the Sequence Listing are hereby incorporated by reference.

BACKGROUND OF THE INVENTION

Field of the Invention

The disclosure pertains to the design and production of a stable, engineered plasmid DNA (pDNA) SARS-CoV-2 spike (S) protein vaccine that induces protective humoral and cellular responses against SARS-CoV-2.

Description of Related Art

In the 21st century, three coronaviruses that have evolved an ability to cross the species barrier and infect humans have been identified: severe acute respiratory disease syndrome coronavirus (SARS-CoV), Middle East respiratory syndrome (MERS)-CoV, and, most recently, SARS-CoV-2.

SARS-CoV-2 entry is dependent on its surface glycoprotein, the spike (S) protein, which binds to the angiotensin-converting enzyme 2 (ACE2) receptor on host cells. The spike protein is a trimeric type 1 transmembrane protein with each monomer consisting of a receptor binding subunit (S1) and a membrane-fusion subunit S2. As with all human coronaviruses, the S protein is a primary antigenic determinant responsible for eliciting antibodies that prevent viral entry and fusion with a host cell membrane.

Human immunity against coronaviruses is mediated by the production of neutralizing antibodies at levels that are sufficient to confer protection against reinfection. S protein-specific antibodies are detected 1-2 weeks after either natural infection or vaccination. However, the durability of these antibodies following infection with human coronaviruses varies. For example, S protein antibodies elicited by the endemic alpha or beta coronaviruses wane within 12 months, whereas antibodies elicited after infection with SARS-CoV or MERS-CoV can last between 12 and 36 months.

Recent studies have shown that the magnitude of neutralizing antibody responses against SARS-CoV-2 is dependent on disease severity. However, the persistence of these S protein antibodies and whether they can provide long-lasting immunity has yet to be determined.

Resolving this issue is critical for vaccine development, as insufficient neutralizing antibody levels induced after immunization presents a major hurdle for generating effective immunity.

Current vaccines to SARS-CoV include mRNA-based Pfizer BioNTech and Moderna vaccines both of which use lipid nanoparticles to encapsulate the mRNA payload. For example, the Moderna vaccine contains 1,2-distearoyl-sn-glycero-3-phosphocholine, cholesterol, and polyethylene glycol-lipid and the Pfizer vaccine contains similar lipids. The Pfizer vaccine also incorporates 1-methylpseudouridine to reduce immunogenicity of the mRNA and increase its translation rate. RNA vaccines are often difficult to transport and store and often must be kept frozen or refrigerated. Moreover, such vaccines are fragile and are prone to degradation, therefore, these vaccines are often encapsulated, such as the Pfizer and Moderna vaccines. Lipid components have been associated with anaphylaxis and rare allergic reactions in some recipients of these vaccines.

Adenovirus vector vaccines include Oxford-Astrazenica (currently Vaxzevria), Sputnik V, Convidicea, and Johnson & Johnson COVID-18 vaccines. The Oxford-AstraZeneca vaccine (ChAdOx1) utilizes an adenovirus vector derived from the chimpanzee, incorporating genetic sequences that instruct cellular machinery to produce the full-length spike protein of SARS-CoV-2. The Convidicea (CanSino Biologics) and Johnson & Johnson one-dose vaccines use Adenovirus 5 (Ad5) and 26 (Ad26), respectively. Adenovirus-based vaccine can lack efficacy in subjects who have pre-existing antibodies to adenoviruses. Further, although rare, there is a possible link with occurrence of blood clot in AstraZeneca vaccine recipients. Most of these cases have occurred in vaccine recipients under the age of 55 and they were mostly women (7 DIC and 18 CVST cases). The link with rare blot clot was observed after the administration of first dose of AstraZenca vaccine. In April 7th, the UK regulators have restricted the use of AstraZeneca to individuals between the age of 18-30 and these were recommended to use alternative vaccines.

Plasmid or pDNA vaccines may offer several unique advantages. These include a high safety profile, economy and cost-effectiveness compared to other vaccines, and ability to be robustly and rapidly manufactured. For example, biosafety level 3 (BSL-3) facilities are not required for the generation of pDNA vaccines. In addition, a pDNA vaccine is thermally stable over extended period of time and pDNA vaccines are more thermostable than mRNA-based vaccines that require transport and storage at low temperatures. Further, unlike with live attenuated and inactivated vaccine where the whole virus is administered to the body, DNA vaccine utilizes a single gene of interest that is responsible for eliciting immunity against a given virus. Therefore, there is no risk for infection or reversion of the virus upon pDNA vaccine administration. However, prior studies indicated that efficacy of a pDNA vaccine depends on the virus type causing the infection and on how a virus interacts with the immune system.

Consequently, the inventor sought to evaluate whether a pDNA-based vaccine could be designed that would provide a high level of protection against infection by SARS-CoV-2. Their pre-clinical studies evaluated the immunogenicity of representative SARS-CoV-2 pDNA vaccines that targeted full length S protein as well as the S1 subunit of S protein. The side-by-side efficacy of these constructs was determined based on induction of humoral, antibody-medicated responses as well as by production of interferon-γ, which is a cytokine important for innate and adaptive immunity against viral pathogens and an inducer of Class II MHC expression.

BRIEF SUMMARY OF THE INVENTION

The disclosure is directed to design, synthesis, production, and immunological evaluation of pDNA vaccines that induce humoral and cellular immune responses against SARS-CoV-2, the causative agent of COVID-19. The pDNA vaccines target SARS-CoV-2 S protein determinants, are thermostable and do not require encapsulation; their production is highly scalable and they may be produced rapidly and in large quantities. The pDNA vaccines may be conveniently administered intramuscularly without the need for electroporation or use of a gene gun.

Other embodiments of this technology include, but are not limited to the following.

A plasmid DNA that comprises the nucleic acid sequence of SEQ ID NO: 1 or 3 or a fragment thereof, which encodes an immunogenic portion of SARS-CoV-2 S1 protein; or that comprises a nucleic acid sequence at least 99% identical to SEQ ID NO: 1 or 3 or a fragment thereof, which encodes an immunogenic portion of SARS-CoV-2 S1 protein. In a preferred embodiment, the amino acid sequence is selected and modified according to a selected human codon usage, GC content, and other criteria for selection of the modified DNA sequence.

The plasmid DNA typically encodes a protein having the amino acid sequence of SEQ ID NO: 7 or encodes a portion thereof, such as an S1 or S2 segment or other immunogenic segment.

In some embodiments it may encode a protein that is at least 95, 96, 97, 98, 99 or >99% identical to the protein of SEQ ID NO: 7 or an immunogenic segment thereof. Typically the plasmid DNA will comprise one or more enhancements to the DNA sequence as disclosed herein.

In one embodiment, the plasmid DNA encodes a full-length S protein.

In another embodiment, the plasmid DNA encodes an S protein or fragment thereof comprising a receptor binding domain (RBD).

In one embodiment, the plasmid DNA encodes an S protein or fragment thereof that lacks all or part of the S2 domain.

In some embodiments, the plasmid DNA encodes an S protein or fragment thereof that lacks at least one of a fusion peptide (FP), a heptad repeat region 1 (HR1), a heptad repeat region 2 (HR2), a transmembrane domain (TM) or a cytoplasmic domain.

In some embodiments the plasmid DNA encodes an S protein consisting of the S1 protein.

In some embodiments, the plasmid DNA may encode a variant full-length S protein or S1 protein that comprises 1, 2, 3, 4, 5, 6, 7, 8, 9, 10 or more amino acid residue deletions, substitutions, or additions to the amino acid sequence described by SEQ ID NO: 7; or that encodes an S protein or S1 protein that is at least 95, 96, 97, 98, 99 or <100% identical to that of SEQ ID NO: 7. In such embodiments, the plasmid DNA insert encoding S or S1 proteins, variants thereof, or immunogenic fragments thereof typically comprise one, two, three or more enhancements as disclosed herein. Such enhancements include, but are not limited to, differences in number or location of CpG sites, CAI, or GC content.

In further embodiments, the plasmid DNA encodes a number or distribution of CpG sites that differs compared to the CpG sites of the polynucleotide of SEQ ID NO: 1 or 3 (gene inserts) or in a plasmid comprising SEQ ID NOS: 2 or 4 (constructs), and which typically differs from that of a corresponding polynucleotide sequence described by SEQ ID NO: 6 (Wuhan Hu 1).

In some embodiments, the plasmid DNA comprises a number of CpG sites that is fewer or that is greater than the number of CpG sites in the polynucleotide of SEQ ID NO: 1 or 3 or in the plasmid comprising SEQ ID NOS: 2 or 4 and which typically differs from that of a corresponding polynucleotide sequence described by SEQ ID NO: 6 (Wuhan Hu 1).

In other embodiments, the plasmid DNA has a codon adaptation index (CAI) for the nucleic acid encoding the immunogenic portion of the S or S1 protein that ranges from 0.91, 0.92, 0.93, 0.94, 0.95, 0.96, 0.97, 0.98, 0.99, to 1.00 and which typically differs from that of a corresponding polynucleotide sequence described by SEQ ID NO: 6.

In some embodiments, the plasmid DNA has a GC content in the nucleic acid encoding the immunogenic portion of the S or S1 protein ranging from 50, 51, 52, 53, 54, 55, 56, 57, 58, 59 to 60% and which typically differs from that of a corresponding polynucleotide sequence described by SEQ ID NO: 6.

In preferred embodiments, the plasmid DNA comprises an enhancer-promoter of mammalian origin, such as a CMV enhancer-promoter of mammalian origin.

In some embodiments, thee plasmid DNA comprises a pcDNA3.1(+) vector.

In one embodiment, the plasmid DNA is S.opt.FL.

In one embodiment, the plasmid DNA is S1.opt.

Another aspect of the invention is directed to a composition comprising the plasmid DNA as disclosed herein and a pharmaceutically acceptable carrier or adjuvant. Preferably, the plasmid DNA is not encapsulated or is lipid-free or polyethylene glycol (PEG)-free.

Another aspect of the disclosure is directed to a method for inducing humoral and/or cellular immunity to infection by SARS-Cov-2 comprising administering the DNA vaccine as disclosed herein to a subject in need thereof. In some embodiments of this method the vaccine is administered as two, three, four or more intramuscular injections at intervals of one to three weeks. Preferably, the pDNA is administered to a human subject, but in some cases, may be administered to an animal susceptible to infection by SARS-CoV-2 or an animal vector or carrier of this virus. The pDNA may be administered to mammals such as simians, dogs, cats, camels, mink, or bats or other animals known to carry or transmit coronaviruses.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 3A. Schematic of the C57BL/6 mice immunization with SARS-CoV-2 vaccines. Immunization groups and doses for the plasmid (p)DNA vaccines. All immunizations were received intramuscularly with 100 μg per dose, except the phosphate-buffered saline (PBS) control group.

The highest dilution that gave an optical density (OD) 450 twofold higher than that of the prebleed sera (week 0) was designated as the antibody endpoint titer in the graphs above. Antibody titers were expressed as mean endpoint titers; standard error of the mean (SEM) for each vaccine group with an individual scatter dot plot (n=6). Data were compared by one-way ANOVA followed by Tukey's multiple comparison test. ns: no significant difference. The asterisks refer to the level of significance: ****$p<0.0001$; ns: no significant difference.

Figure 5B:
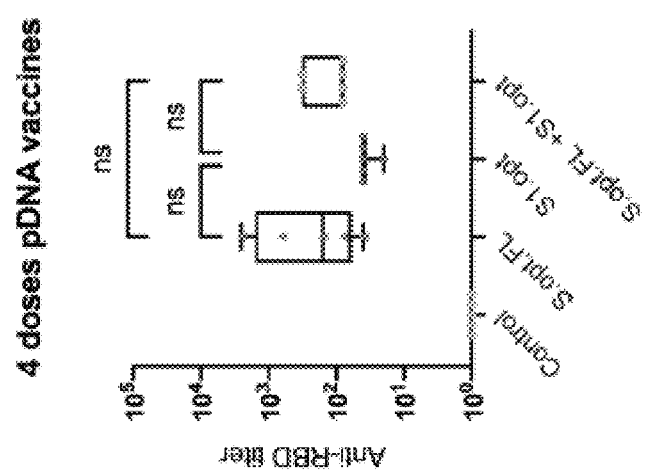
Figure 5A:
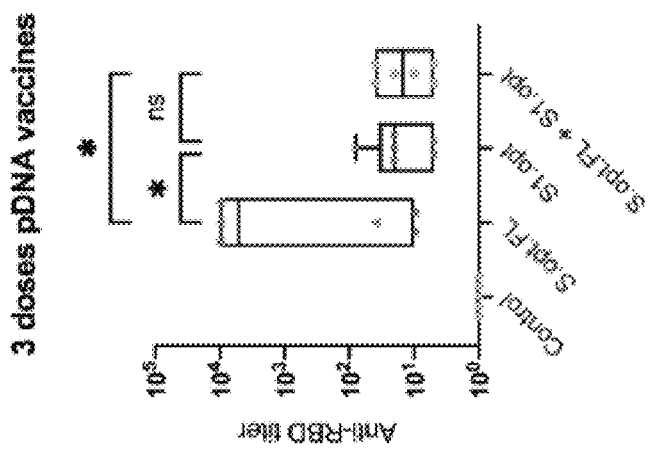

FIG. 5A. Box-and-whisker plot of surrogate virus neutralization test (sVNT). Titer of antireceptor-binding domain (RBD) IgG antibodies from serially diluted mice vaccinated sera taken 2 weeks after the third immunization.

FIG. 5B. Box-and-whisker plot of surrogate virus neutralization test (sVNT). Titer of anti-RBD IgG antibodies from serially diluted mice vaccinated sera taken 2 weeks after the fourth immunization. Cutoff titer was calculated as the serum highest dilution showing a cutoff value >20%. Data were analyzed with one-way ANOVA with Tukey's multiple comparison test. The asterisks refer to the level of significance: *$p<0.033$; ns: no significant difference.

Figure 6:
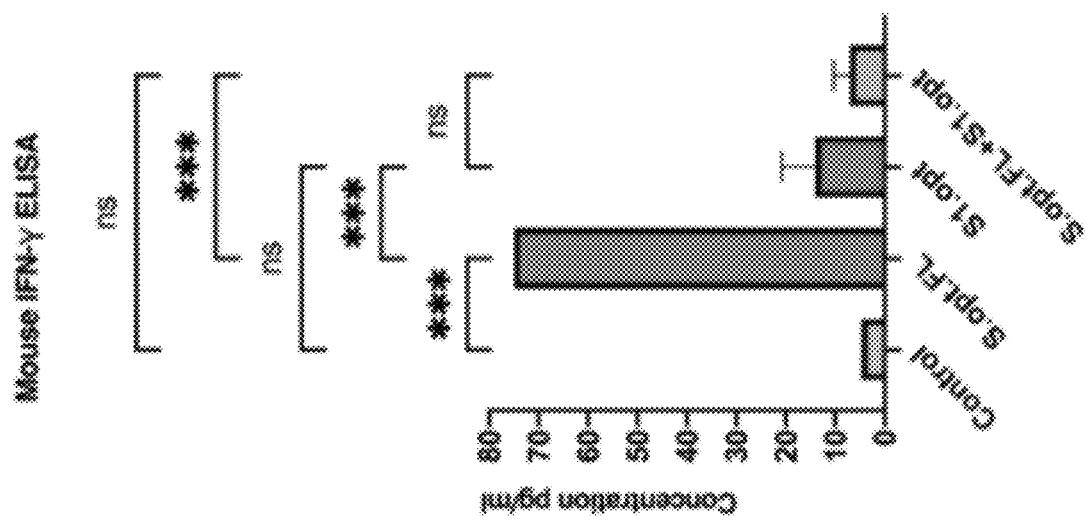

FIG. 6. IFN-γ responses following C57BL/6 mice vaccinations. Comparison of serum IFN-γ levels in each of the vaccine constructs (S.opt.FL, S1.opt, and S.opt.FL+S1.opt) 2 weeks following second immunization in each vaccine construct using pooled mice sera from each group. Endpoint concentration was determined by titers expressed (mean±SD). Data were analyzed with one-way ANOVA with Tukey's multiple comparison test. The asterisks refer to the level of significance: ***$p<0.0002$; ns: no significant difference.

FIG. 7 shows a micrograph of S protein trimers on the surface of SARS-CoV-2.

FIGS. 8A and 8B illustrate the role of S protein in viral attachment and invasion.

DETAILED DESCRIPTION OF THE INVENTION

One aspect of the invention is directed to a pDNA or pDNA vaccine that induces protective humoral and/or cellular responses against SARS-CoV-2 S protein epitopes and to methods using the pDNA to prevent or treat SARS-CoV-2 infection. Surprisingly, it has been found that particular modifications to DNA encoding full-length S protein or the S1 subunit of S protein, enhance vaccine efficacy and stability and specific pDNA vectors are disclosed herein that have been demonstrated to induce immune responses targeting SARS-CoV-2.

SARS-CoV-2 Spike (S) protein. The total length of SARS-CoV-2 S is 1273 aa and consists of a signal peptide (amino acids 1-13) located at the N-terminus, the S1 subunit (14-685 residues), and the S2 subunit (686-1273 residues); the last two regions are responsible for receptor binding and membrane fusion, respectively. In the S1 subunit, there is an N-terminal domain (H-305 residues) and a receptor-binding domain (RBD, 319-541 residues); the fusion peptide (FP) (788-806 residues), heptapeptide repeat sequence 1 (HR1) (912-984 residues), HR2 (1163-1213 residues), TM domain (1213-1237 residues), and cytoplasmic tail (1237-1273 residues) comprise the S2 subunit. S protein trimers visually form a characteristic bulbous, crown-like halo surrounding the viral particle. Based on the structure of coronavirus S protein monomers, the S1 subunit forms the globular head while S2 subunits forms the stalk region. FIGS. 7 and 8 illustrate S protein and S protein mediated attachment and invasion of a host cell.

S protein polynucleotide or polypeptide variants. In some embodiments, the plasmid DNA encoding the segment of S protein, including but not limited to, full-length S protein or the S1 subunit of S protein or an immunogenic segment of S protein, may comprise an polynucleotide sequence that is at least 95, 96, 97, 98, 99 or <100% identical to SEQ ID NO: 1 or 3 or have 1, 2, 3, 4, 5, 6, 7, 8, 9, 10 or more deletions, substitutions, or insertions of nucleotides to a sequence of SEQ ID NO: 1 or 3, and encode a protein that comprises at least one epitope of S protein.

In some embodiments, the plasmid DNA may encode a variant full-length S protein or S1 protein that comprises 1, 2, 3, 4, 5, 6, 7, 8, 9, 10 or more amino acid residue deletions, substitutions, or additions to the amino acid sequence encoded by SEQ ID NOS: 1, 2, 3, or 4 or that encodes an S protein or S1 protein that is at least 95, 96, 97, 98, 99 or <100% identical to that encoded by SEQ ID NOS: 1, 2, 3 or 4.

BLASTN may be used to identify a polynucleotide sequence having at least 70%, 75%, 80%, 85%, 87.5%, 90%, 92.5%, 95%, 97.5%, 98%, 99% or <100% sequence identity to a reference polynucleotide such as a polynucleotide encoding an S protein, antigenic or immunogenic S protein fragment, or S1 subunit. A representative BLASTN setting modified to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to ≤hypertext transfer protocol secure://blast.ncbi.nlm.nih.gov/Blast.cgi?PROGRAM=blastn&PAGE_TYPE=BlastSearch& LINK_LOC=blasthome≥ (last accessed Mar. 23, 2021).

BLASTP can be used to identify an amino acid sequence having at least 70%, 75%, 80%, 85%, 87.5%, 90%, 92.5%, 95%, 97.5%, 98%, 99% or <100% sequence identity, or similarity to a reference amino acid, such as an S protein, S1 subunit protein, or antigenic or immunogenic segment of S protein, amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: ≤hypertext transfer protocol secure:// blast.ncbi.nlm.nih.gov/Blast.cgi?PROGRAM=blastp&PAGE_TYPE=BlastSearch&LINK_LOC=blasthome> (last accessed Mar. 23, 2021).

The inventor made several modifications to the SARS-CoV-2 S protein and 51 protein nucleic acid sequences to attain these benefits.

Codon Adaptation Index (CAI) is the most widespread technique for analyzing codon usage bias. As opposed to other measures of codon usage bias, such as the effective number of codons (Nc), which measure deviation from a uniform bias (null hypothesis), CAI measures the deviation of a given protein coding gene sequence with respect to a reference set of genes. CAI is used as a quantitative method of predicting the level of expression of a gene based on its codon sequence; see Sharp, Paul M. & Li, Wen-Hsiung, *The codon adaptation index-a measure of directional synonymous codon usage bias, and its potential applications*, NUCLEIC ACIDS RESEARCH, 1987, 15 (3): 1281-1295 (incorporated by reference). Software suitable for optimizing codon usage is known and may be used to optimize codon usage in a pDNA construct or a segment thereof, such as an immunogenic portion of the S protein of SARS-CoV-2; see Optimizer available at ≤hypertext transfer protocol://genomes._urv.cat/OPTIMIZER/≥(last accessed Mar. 17, 2021). Codon usage frequencies for various organisms are known and are also incorporated by reference to hypertext transfer protocol://genomes.urv.cat/OPTIMIZER/CU_human_nature.html or to the Codon Usage Database at worldwide web.kazusa.or.jp/codon/ (last accessed Mar. 17, 2021). A pDNA construct or its elements as described herein may have a CAI ranging from 0.8, 0.90, 0.91, 0.92, 0.93, 0.94, 0.95, 0.96, 0.97, 0.98, 0.99, 1.0, preferably about 0.94. These CAI percentages are considered favorable in terms of level of gene expression from the pDNA.

Codon Adaptation Index (CAI) is the most widespread technique for analyzing codon usage bias. As opposed to other measures of codon usage bias, such as the effective number of codons (Nc), which measure deviation from a uniform bias (null hypothesis), CAI measures the deviation of a given protein coding gene sequence with respect to a reference set of genes. CAI is used as a quantitative method of predicting the level of expression of a gene based on its codon sequence; see Sharp, Paul M. & Li, Wen-Hsiung, *The codon adaptation index-a measure of directional synonymous codon usage bias, and its potential applications*, NUCLEIC ACIDS RESEARCH, 1987, 15 (3): 1281-1295 (incorporated by reference). Software suitable for optimizing codon usage is known and may be used to optimize codon usage in a pDNA construct or a segment thereof, such as an immunogenic portion of the S protein of SARS-CoV-2; see Optimizer available at hypertext transfer protocol://genomes_urv.cat/OPTIMIZER/(last accessed Mar. 17, 2021). Codon usage frequencies for various organisms are known and are also incorporated by reference to hypertext transfer protocol://genomes.urv.cat/OPTIMIZER/CU_human_nature.html or to the Codon Usage Database at worldwide web.kazusa.orjp/codon/(last accessed Mar. 17, 2021). A pDNA construct or its elements as described herein may have a CAI ranging from 0.8, 0.90, 0.91, 0.92, 0.93, 0.94, 0.95, 0.96, 0.97, 0.98, 0.99, 1.0, preferably about 0.94. These CAI percentages are considered favorable in terms of level of gene expression from the pDNA.

In some embodiments, the techniques described above are used to design the polynucleotide sequence of the pDNA or pDNA encoding S protein determinants.

GC content. In molecular biology and genetics, GC-content (or guanine-cytosine content) is the percentage of nitrogenous bases in a DNA or RNA molecule that are either guanine (G) or cytosine (C). This measure indicates the proportion of G and C bases out of an implied four total bases, also including adenine and thymine in DNA and adenine and uracil in RNA. GC-content may be given for a certain fragment of DNA or RNA or for an entire genome. When it refers to a fragment, it may denote the GC-content of an individual gene or section of a gene (domain), a group of genes or gene clusters, a non-coding region, or a synthetic oligonucleotide such as a primer. While high GC content may stabilize a DNA construct, its effects on uptake of a pDNA vaccine, structural effects on transcribed mRNA, and expression level of a protein expressed by pDNA cannot be accurately predicted. A pDNA construct as described herein may have a GC content ranging from about 30 to 70%, for example, about 50, 51, 52, 53, 54, 55, 56, 57, 58, 59 or 60, preferably about 55-56%.

CpG dinucleotide content. The CpG sites or CG sites are regions of DNA where a cytosine nucleotide is followed by a guanine nucleotide in the linear sequence of bases along its 5'→3' direction. CpG sites occur with high frequency in genomic regions called CpG islands (or CG islands). Nucleic acids containing CpG motifs can activate host innate and acquired immune responses. Further characterization of CpG sequences which may be used in conjunction with the pDNA vaccine disclosed herein are incorporated by reference to H. L. Davis, Dev Biol (Basel) 2000; 104:165-9.

RNA stability/instability motifs (AU-rich elements, ARE). The presence of AU-rich elements in some mammalian mRNAs tends to destabilize those transcripts through the action of cellular proteins that bind these sequences and stimulate poly(A) tail removal. Adenylate-uridylate-rich elements (AU-rich elements; AREs) are found in the 3' untranslated region (UTR) of many messenger RNAs (mRNAs) that code for proto-oncogenes, nuclear transcription factors, and cytokines. AREs are defined as a region with frequent adenine and uridine bases in a mRNA. FIG. 1 describes the modified sequence containing modifications described below.

Cryptic splicing sites can be present at the mRNA level. A cryptic splice site is a mRNA sequence that has the potential for interacting with the spliceosome. Mutations, including splice site mutations, in the underlying DNA or errors during transcription can activate a cryptic splice site in part of the transcript that usually is not spliced.

Premature polyA sites may occur in a sense strand encoding mRNA. These A-rich coding strands result in premature polyadenylation and aberrant mRNA splicing.

Repeat sequences and Secondary mRNA structures such as hairpins, loops, and stems can cause interference with the translation of protein.

In addition to modification of the S protein nucleic acid sequences, the inventor sought and found that particular vectors were suitable for expression of the modified S protein and S1 subunit nucleic acid sequences.

Plasmid vectors. Description pcDNA™3.1(+) and pcDNA™3.1(−) are commercially available vectors derived from pcDNA 3 and designed for high-level stable and transient expression in mammalian hosts. High-level stable and non-replicative transient expression can be carried out in most mammalian cells. In some embodiments, other vectors may be selected, for example, based on the promoters they contain or on other features contributing to their genetic stability when administered to a subject. Promoters which may be used to express or enhance expression of S protein determinants include SV40, RSV and CMV promoters. Additional modifications to improve expression rates include the insertion of enhancer sequences, synthetic introns, adenovirus tripartite leader (TPL) sequences and modifications to the polyadenylation and transcriptional termination sequences; see Alarcon, J. B., et al., Parasitology, 1999, 42, 343-410 which is incorporated by reference.

Advantageously, it was found that the pDNA vaccine as disclosed herein was thermostable and did not require encapsulation in order to induce protective humoral and cellular responses against SARS-CoV-2./

Carriers, Excipients and Adjuvants. In a preferred embodiment, the pDNA is not encapsulated and it is not necessary to admix it with a polymer, a liposome, or particles (e.g. microparticles or nanoparticles). For example, it is not necessary to form particles of pDNA and cationic polymers such as polyamines (e.g., polyethyleneimine (PEI), polyhistidine, carboxymethylcellulose (CMC), putrescine, spermidine, or spermine), laminar or multilaminar liposomes, or particles of calcium phosphate, or other compositional forms such as an emulsion, a microcapsule, a microsphere, or a nanoparticle Compositions. Pharmaceutical compositions of the present disclosure comprise an effective amount of pDNA formulation disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 21st edition, 2005, incorporated herein by reference. Moreover, for animal, mammal or human administration, it will be understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it needs to be sterile for such routes of administration as injection.

It was also found that the pDNA vaccine as disclosed herein could be easily and conveniently administered intramuscularly.

Routes of administration. Preferably, the pDNA compositions disclosed herein are administered intramuscularly. Other modes for pDNA administration include electroporation and gene gun; see Wang, S. et al., DNA immunization, Curr. Protoc. Microbiol., 2013, 31, 18.3.1-18.3.24, incorporated by reference.

Alternatively, the compositions disclosed herein can be administered intravenously, intradermally, transdermally, intrathecally, intraarterially, intraperitoneally, intranasally, intravaginally, intrarectally, topically, subcutaneously, mucosally, in utero, orally, topically, locally, via inhalation (e.g., by aerosol inhalation, dry powder inhalation), by injection, by infusion, by continuous infusion, by localized perfusion bathing target cells directly, via a catheter, via a lavage, in cremes, in lipid compositions (e.g., in liposomes), or by other method or any combination of the forgoing as would be known to one of ordinary skill in the art (see, for example, Remington's Pharmaceutical Sciences, 2003, incorporated herein by reference).

In certain embodiments, a composition herein and/or additional agents is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with edible carrier that can be assimilated.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally.

Solutions of the compositions disclosed herein as free bases or pharmacologically acceptable salts may be prepared in water suitably mixed with a surfactant, such as hydroxypropylcellulose. In some embodiments, agents such as EDTA or EGTA (e.g., Tris-EDTA buffer) are incorporated to prevent degradation of the pDNA by scavenging divalent cations. Other stabilizers including malic acid, ethanol, and Pluronic F-68 are known in the art and are incorporated by reference to Y. Zeng, et al., Journal of Pharmaceutical Sciences, March 2011, 100, 904-914.

Dispersions of the pDNA may be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the pDNA compositions in the required amount in the appropriate solvent with various of the other ingredients enumerated above, as required, followed by filter sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (e.g., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the pDNA compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in t its entirety). Likewise, the delivery of drugs using intranasal microparticle resins (Takenaga et al., JOURNAL OF CONTROLLED RELEASE, 1998, 52, 81-87) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated by reference), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Dosage. The actual dosage amount of a composition disclosed herein administered to an animal or human patient can be determined by physical and physiological factors such as body weight or surface area, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.01, 0.02, 0.05, 0.1, 0.2, 0.5 or 1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/ kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Dosing Regimen. One skilled in the medical and immunological arts may select an appropriate dosing regimen. To enhance the magnitude of antibody responses against SARS-CoV-2, preferably, a regimen comprises administering three separate doses of pDNA intramuscularly over a four week period, preferably at 2 week intervals (0, 2, 4 weeks). Alternatively, the pDNA vaccine may be administered less frequently, for example, a two dose of the pDNA may be given to healthy individuals intramuscularly.

EXAMPLES

Figure 1A:
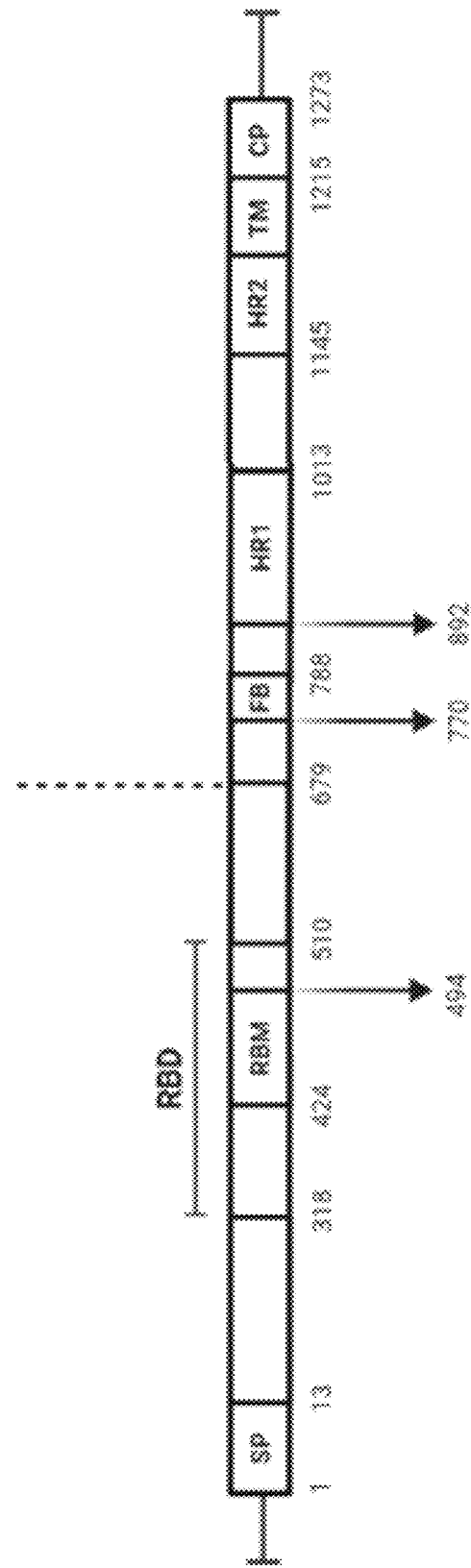
FIG. 1A: Schematic of the severe acute respiratory syndrome coronavirus 2 (SARS-CoV-2) spike (S) glycoprotein. The primary structure of S protein with its S1 and S2 subunits including signal peptide (SP), receptor binding domain (RBS), fusion peptide (FB/FP), heptad repeats (HR1/HR2), transmembrane (TM), and cytoplasmic tail (CP/CT).

Construct Modification and Vaccination Strategy. The S glycoprotein of SARS-CoV is composed of two subunits, S1 and S2. The S1 subunit consists of four domains, namely, the N-terminal domain (NTD), the C-terminal domain (CTD), and subdomains II and I. In addition, the S1 subunit contains the receptor binding domain (RBD), an essential component required for binding to the human (h)ACE2 receptor on the host cell (FIG. 1A).

The S2 subunit consists of the fusion peptide (FP) domain, heptad repeats (HR) 1 and 2, the transmembrane domain (TM), and the cytoplasmic tail (CT). These elements are necessary for the fusion of SARS-CoV-2 with the host cell membrane (FIG. 1A).

Figure 1B:
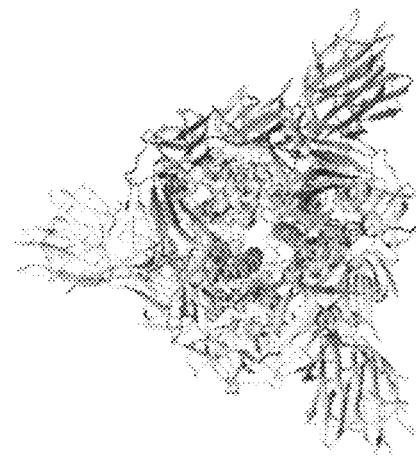
FIG. 1B. Side and top view of the three-dimensional structure of the trimeric spike protein in the perfusion confirmation. Image created from the structure with Protein Data Bank (PDB) identifier VXX6 (incorporated by reference).
Figure 1B:
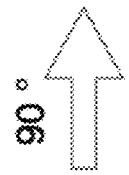
Figure 1B:
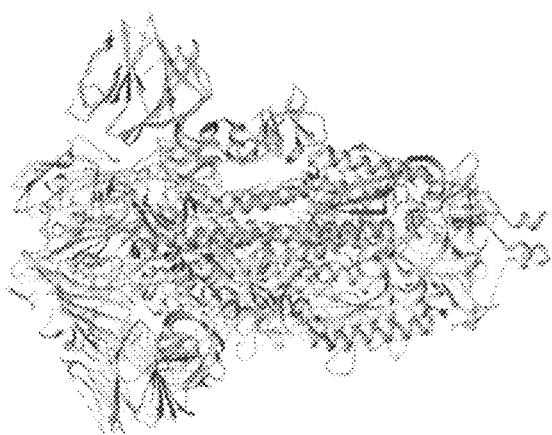

The S protein of coronaviruses is a trimeric type I transmembrane, and each monomer consists of S1 and S2 subunits (FIG. 1B).

Figure 2A:
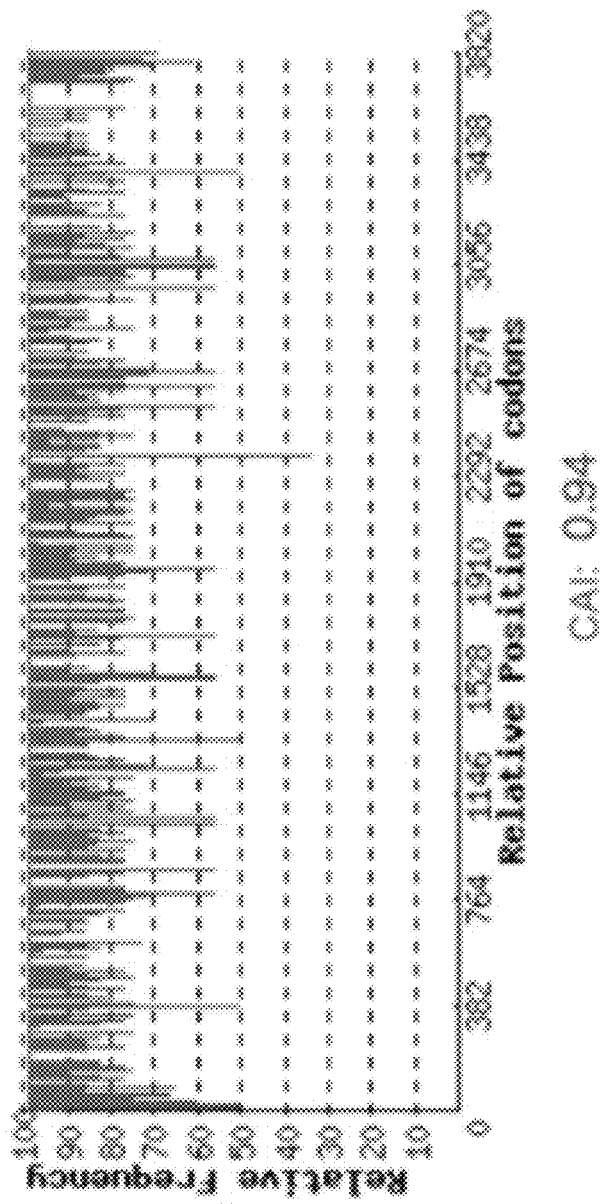
FIG. 2A. Modification of the full-length SARS-CoV-2 spike gene. Distribution of codon usage frequency of the spike (S) protein gene. Codon Adaptation Index (CAI)=0.94.

Two vaccine constructs were tested in this study: pDNA S.opt.FL containing the full-length S gene and pDNA S1.opt including only the globular head, S1 subunit. The codons of S.FL gene were changed to mammalian codon preference (*Homo sapiens*) to enhance the gene expression in mammalian cells (FIGS. 2A-C) and were subsequently synthesized and inserted into pcDNA 3.1(+).

Furthermore, the S1.opt was generated from S.FL via mutagenesis study.

Figure 2B:
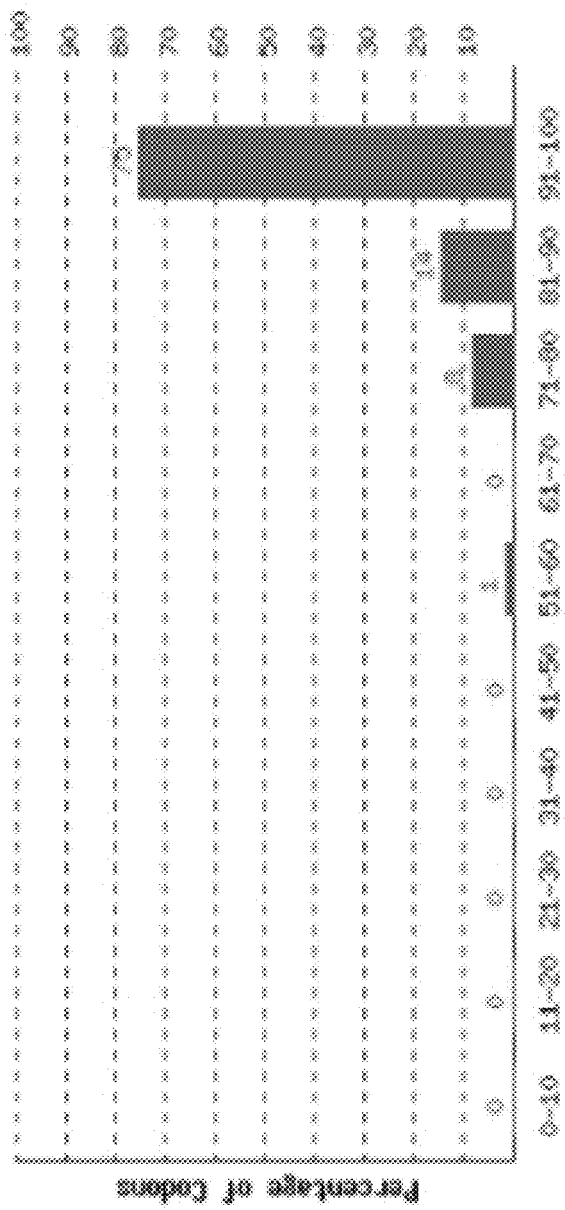
FIG. 2B. Codon distribution percentage computed as codon quality group.
Figure 2C:
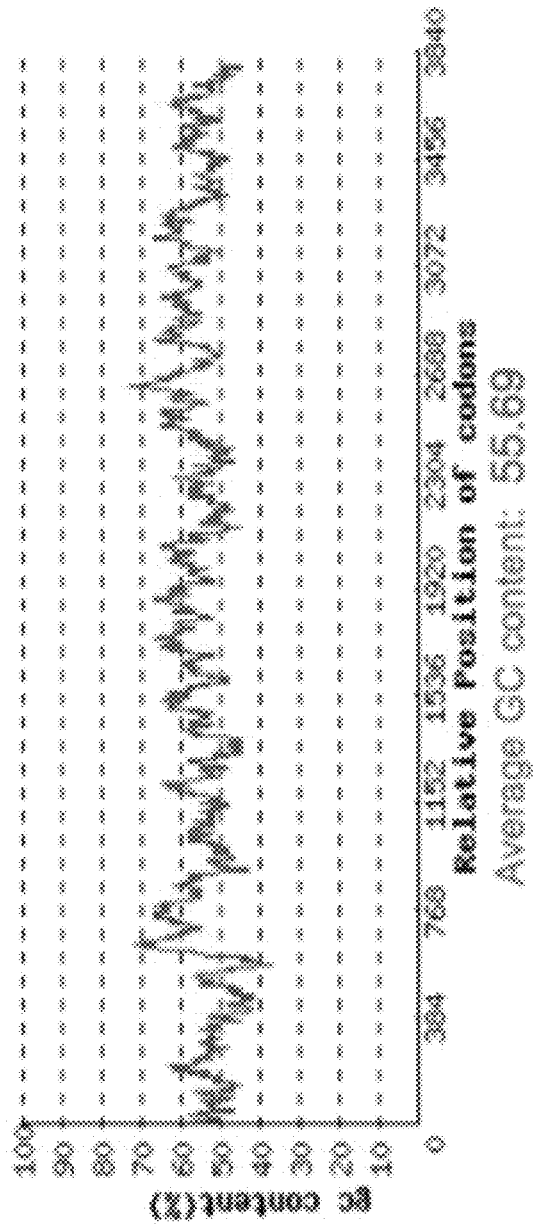
FIG. 2C. GC content adjustment with average equal to 55.69.
Figure 2D:
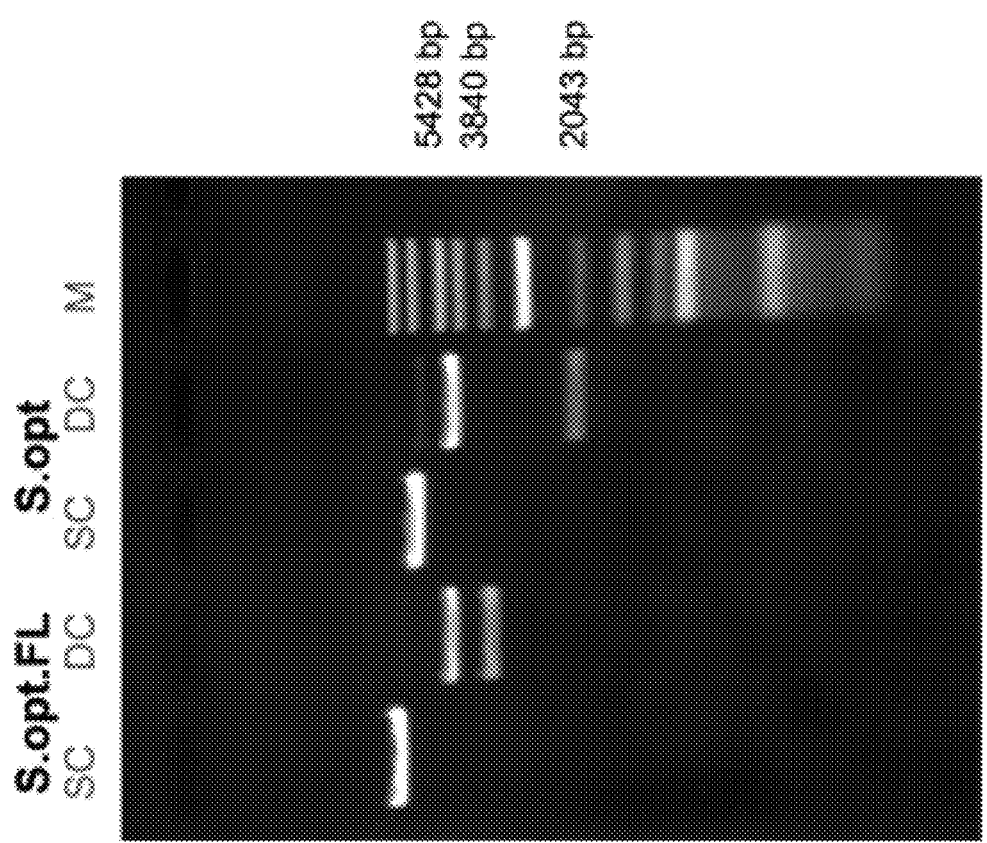
FIG. 2D. Restriction analysis of the S.opt.FL and S1.opt constructs using single-cut (SC) digestion with BamHI and double-cut (DC) digestion with BamHI and NheI.

Both sequences were tested for the correct gene size (FIG. 2B).

Mice were divided into seven groups (n=6 per group); the first group received pDNA S.opt.FL, the second group received pDNA S1.opt, and the third group receive done dose of pDNA S.opt.FL followed by two doses of pDNA S1.opt.

These groups each received three doses of vaccine. Group four received pDNA S.opt.FL, group five received pDNA S1.opt, and group six received one dose of pDNA S.opt.FL followed by three doses of pDNA S1.opt; these groups each received four doses of vaccine.

Group seven was the control group and received only phosphate-buffered saline (PBS) (FIG. 3A). A mouse from the control group died prior to first immunization and another mouse from group 4 died after first immunization.

Immunogenicity in Mice: Production of Binding Antibodies. All C57BL/6 mice were vaccinated intramuscularly (IM) at 6-8 weeks of age with the pDNA vaccines or with the PBS control; blood was collected at 2 week intervals.

Figure 3B:
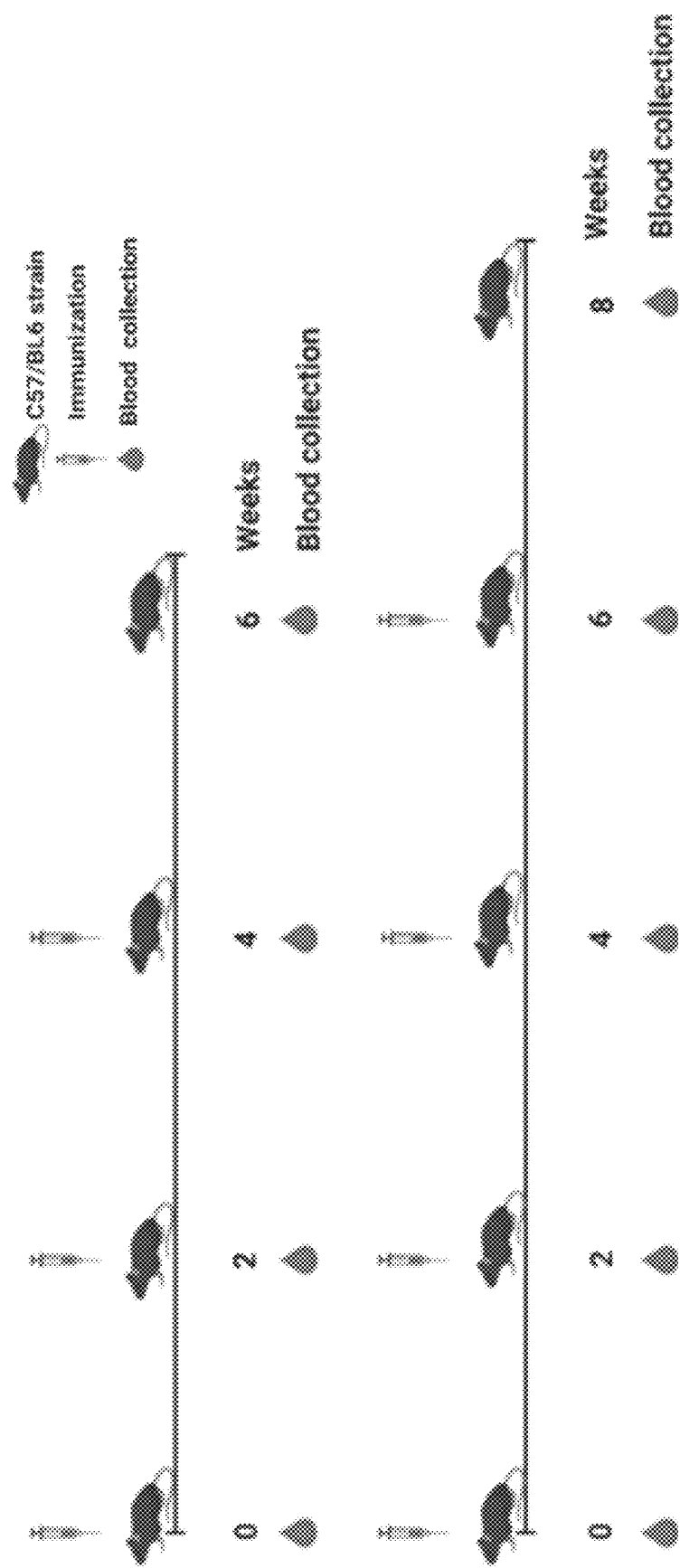
FIG. 3B. The bleeding and immunization regime for the C57BL/6 mice.

Total immunoglobulin G (IgG) antibodies against the S protein were measured in serum samples collected 2 weeks after the last immunization (FIG. 3B).

Figure 4A:
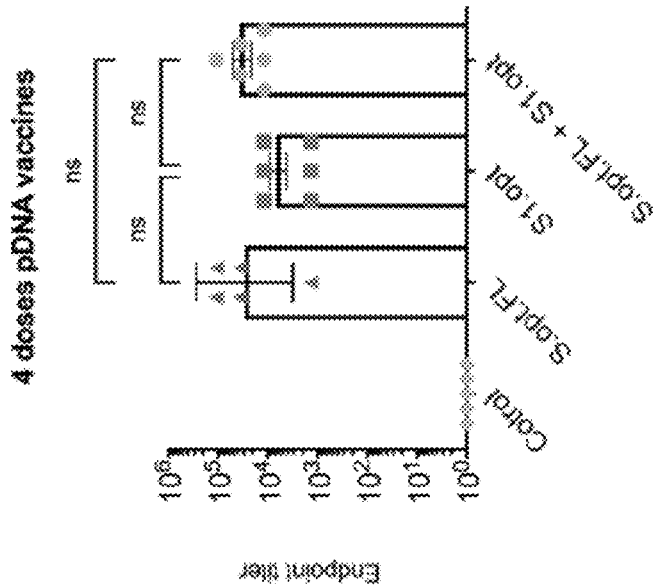
FIG. 4A. Serum endpoint immunoglobulin G (IgG) ELISA titers against autologous full-length spike (S) protein. Total IgG S antibodies were measured in mice sera 2 weeks after the third immunization. Serum starting concentration was 1:50.
Figure 4B:
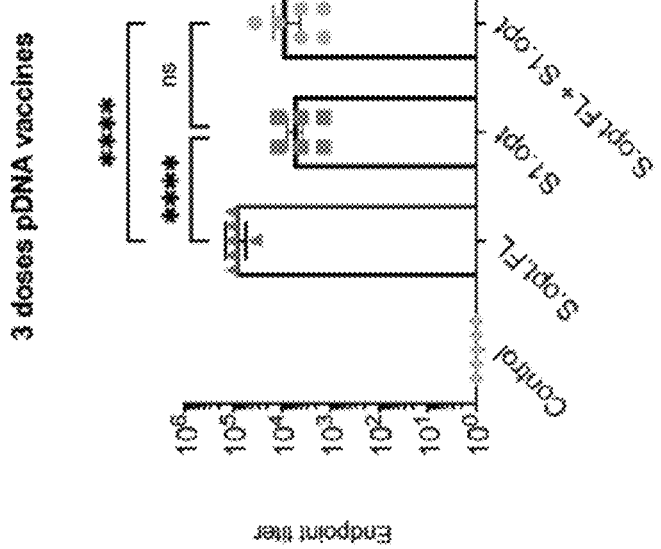
FIG. 4B. Serum endpoint immunoglobulin G (IgG) ELISA titers against autologous full-length spike (S) protein. Total IgG S antibodies were measured in mice sera 2 weeks after the fourth immunization.

The results indicated that sera from all groups of immunized mice, except the PBS control group, contained detectable levels of binding antibodies at weeks 6 and 8 (FIGS. 4A, 4B).

Comparisons among vaccine groups further revealed that mice vaccinated with S.opt.FL pDNA vaccine (groups 1 and 4) generated the highest levels of binding antibodies, with three and four doses of vaccine eliciting equivalent antibody responses (FIGS. 4A,4B).

Mouse groups immunized with the pDNA S1.opt vaccine produced the lowest levels of antibody responses, while the heterologous vaccine produced a moderate immune response (FIG. 4A,4B).

Immunogenicity in Mice: Production of Neutralizing Antibodies. To assess the immunological efficacy of the two pDNA vaccines, a surrogate virus-neutralizing assay was performed. This technique is based on the fact that neutralizing antibodies can block the interaction between the SARS-CoV-2 RBD and the ACE2 receptor.

Neutralization assay results revealed that mice who received three immunization doses with pDNA S.opt.FL produced higher levels of neutralizing antibodies than mice vaccinated with three doses of pDNA S1.opt (FIG. 5A).

Mice immunized with S.opt.FL at weeks 6 and 8 produced similar levels of neutralizing antibodies. It was also found that an additional dose enhanced the levels of neutralizing antibodies; that is, mice who received S.opt.FL priming, followed by the three S1.opt booster doses, had higher antibody responses than those who received only two S1.opt booster doses (FIGS. 5A, 5B).

Interestingly, mice immunized with four doses of S1.opt produced comparable levels of neutralizing antibody responses to immunization with three doses (FIGS. 5A, 5B).

Immunogenicity in Mice: Production of IFN-γ. Recent studies highlighted the role of cell-mediated responses in controlling COVID-19. We, therefore, measured the serum levels of IFN– in mice immunized with our vaccine constructs, as an indicator of innate immunity/cellular immunity.

It was found that consistent with the antibody data, mice immunized with S.opt.FL pDNA vaccine produced significantly higher serum levels of IFN–, relative to the other experimental vaccine groups (FIG. 6).

The pDNA platform is as an attractive strategy for vaccine development during pandemics. This technology is simple and highly scalable. Furthermore, unlike mRNA vaccines that are fragile and require encapsulation to protect from degradation, pDNA vaccines are thermally stable, which is particularly beneficial during vaccine shipment and storage.

Limited data are available on the effect that multiple vaccine doses can have on eliciting potent neutralizing antibodies. The pDNA vaccines designed and produced by the inventor encode the full-length SARS-CoV-2 S gene and S1 as the antigens of interest.

In addition, combining multiple gene inserts in a plasmid vector may interfere with expression of the proteins encoded by these gene inserts; hence, we tested combined administration of the different constructs (S.opt.FL and S1.opt genes) at different doses.

Previous studies on pDNA vaccines against other viral pathogens determined that the optimal dosage required for effective immunity is dependent on the antigen/virus type and how these interact with the immune system. For example, one to two doses of pDNA vaccine are sufficient to produce effective neutralizing antibodies for influenza viruses; however, three to four doses are needed to elicit a sufficient protective immune response in HIV [17].

Neutralizing antibodies against SARS-CoV-2 target the spike RBD known to bind to ACE2 of host cell, thereby blocking viral entry. However, the number of pDNA vaccine doses needed to elicit optimal neutralizing antibody responses to SARS-CoV-2 remains unexplored. The inventor considered that multiple doses of a SARS-CoV-2 pDNA vaccine would be needed to generate an effective SARS-CoV-2 antibody-mediated immune response. Therefore, both a three and four dose regimen of each SARS-CoV-2 pDNA vaccine was used to determine which of these could elicit the most potent neutralizing antibody response.

As shown herein, it was found that three doses of pDNA S.opt.FL vaccine induced the highest levels of neutralizing antibodies, with no added antibody production conferred by the fourth vaccine dose.

In addition, the full-length S protein elicited the most potent immune response, as compared to the pDNA S1.opt vaccine or the S.opt.FL with an S1.opt booster, suggesting that multiple doses of full-length S are needed to elicit high-level immune responses. The inventor consider that non-RBD epitopes may have greater surface accessibility and thus be more immunogenic than some RBD epitopes. Consistent with this observation, mice vaccinated with S.opt.FL elicited higher IFN-production than mice vaccinated with the S1.opt or the combined vaccine. This result is also consistent with the identification of epitopes outside of the S1 domain; see Zheng, et al., Cell Mol. Immunol, 2020 17, 536-538.

The data described herein was obtained following the procedures described below.

Ethics Statement This preclinical study was registered under the Animal Study Registry 10.17590/asr.0000212. Animal protocols were approved by the Institutional Review Board (IRB NO-2020-333-IRMC) at Imam Abdulrahman Bin Faisal University (IAU), and experiments were done in compliance with the institution guidelines.

pDNA Vaccine Constructs. Polynucleotide constructs encoding the full-length S protein (3840 bp) (YP_009724390.1) or its S1 subunit was codon-modified for *Homo sapiens*.

SEQ ID NO: 1 describes the DNA sequence of the gene insert of S.opt.FL which is designated Almansour-I.

SEQ ID NO: 2 describes the DNA sequence of the S.opt.FL construct.

SEQ ID NO: 3 describes the DNA sequence of the gene insert of S1.opt

SEQ ID NO: 4 describes the DNA sequence of the S1.opt construct which is designated Almansour-II.

SEQ ID NO: 5 describes a Kozac sequence.

SEQ ID NO: 6 describes a native DNA sequence encoding SARS CoV-2 Spike protein. This sequence as well as the amino acid sequence it encodes and other information are described by, and incorporated by reference to, NCBI Reference Sequence: NC_045512.2 and to ≤hypertext transfer protocol secure:// www.ncbi.nlm.nih.gov/nuccore/NC_045512.2?reportgenbank&from=21563&to=25384≥ (last accessed May 3, 2021).

SEQ ID NO: 7 describes an amino acid sequence translated from the DNA sequence of SEQ ID NO: 6.

Other modifications that were made include changes to GC % content, mRNA secondary structure, cryptic splicing sites, premature polyA sites, internal Chi sites, ribosomal-binding sites, and RNA stability motifs. For example, the entire S.FL sequence was codon-enhanced. To increase translation initiation a Kozac sequence (comprising SEQ ID NO: 5) was added downstream of the NheI restriction site in the constructs. A Shine-Dalgarno sequence is not required for eukaryotic expression but may be incorporated for use in prokaryotic expression systems.

The designed sequences were chemically synthesized and BamHI and NheI sequences were incorporated upstream and downstream of the S.opt.FL sequence, respectively. The S.opt.FL sequence was inserted into pcDNA3.1 (+) and cloned to further increase the efficiency of translation in eukaryotes. The S1.opt sequence was synthesized by mutagenesis from the template S.opt.FL. A Kozac sequence was added upstream of the coding sequence: (GCCACC SEQ ID NO: 5.

The S.opt.FL was de novo synthesized (GenScript, Piscataway, NJ, USA), and NheI and BamHI restriction sites were incorporated up- and downstream, respectively, of the coding sequence.

The S.opt.FL insert was individually cloned into pcDNA 3.1(+).

The nucleotide sequence of the S.opt.FL construct was confirmed by sequencing. The S1.opt construct (2043 bp) was synthesized by mutagenesis using the synthesized S.opt.FL as a template.

Briefly, a mutagenesis oligo was synthesized and the S.opt.FL pcDNA 3.1(+) was amplified by PCR using the mutagenesis oligo.

The mutagenesis construct was linearized by NheI and BamHI and subsequently ligated.

The construct was transformed into competent cells and was incubated overnight in LB media with ampicillin at 37° C.

A colony was picked and verified by colony PCR and sequencing.

For pDNA vaccine production, each cloned vaccine construct was grown in LB media containing ampicillin and was incubated overnight at 37° C.

A plasmid DNA purification kit (Cat #12163, QIAGEN®) was used to purify each vaccine construct. The purification levels for S.opt.FL and S1.opt, verified at absorbance 260/280, were 1.91 and 1.89, respectively.

Construct lengths were checked by restriction analyses prior to immunization.

Immunizations. C57BL/6 mice, 6-8 weeks of age, were provided by the King Faisal Specialist Hospital and Research Center, Riyadh, Saudi Arabia. These were maintained by the animal house facility at Imam Abdulrahman Bin Faisal University.

Mice were vaccinated intramuscularly (IM) into the tibialis anterior muscle. For each immunization, animals received 100 µg of pDNA in 200 µL of phosphate-buffered saline (PBS), pH 7.4, or the PBS control.

Mice were administered vaccines at multiple sites.

Serum samples were collected prior to the first immunization and 2 weeks after each immunization.

Enzyme-Linked Immunosorbent Assay (ELISA). For ELISAs, 96-well plates (Cat #44-2404-21; Thermo Fisher Scientific, Waltham, MA, USA) were coated with 10 ug/mL of the full-length S antigen (Cat #Z03483-1, Genscript) and incubated overnight at 4° C. Using a 96-well plate washer, plates were washed five times with 300 µL of 1×PBS. For blocking, 2004, of 5% non-fat dry milk in Tris-buffered saline (Blocker BLOTTO Cat #170-6404; Bio-Rad Laboratories, Hercules, CA, USA) was added to each well, and plates were incubated for 1 h at room temperature. Blocked plates were washed five times with 300 μL of 1×PBS, and 100 of serially diluted serum from vaccinated mice was added to each well, followed by incubation for 1 h at room temperature.

After five washes with 300 μL of 1×PBS, 100 μL of goat anti-mouse IgG secondary antibody conjugated to horseradish peroxidase (HRP) (Cat #31430; Invitrogen, Thermo Fisher Scientific) was added to each well, and plates were incubated for 1 h at room temperature. Plates were washed five times with 300 μL of 1×PBS, and 100_L of tetramethylbenzidine (TMB) substrate (Cat #1854050; Thermo Fisher Scientific) was added to all wells, according to the manufacturer's instructions.

Lastly, 100 μL of 2 M sulfuric acid (2M $H_2SO_4$) was added to all wells to stop reactions; optical density (OD) values were read at 450 nm.

Neutralization Assay. The test used to measure antibody neutralization was based on the surrogate virus neutralization test (Cat #L0084; GenScript), a robust assay for testing vaccine efficacy. Briefly, serum samples, as well as positive and negative controls, were serially diluted and incubated with an equal volume (1:1) of diluted HRP-conjugated receptor-binding domain (RBD) a 37° C. for 30 min.

Mixtures were then added to plates coated with ACE2, which were covered and incubated at 37° C. for 15 min. After washing four times with 1×wash solution, 100 μL of TMB was added to each well, and plates were incubated in the dark at room temperature for 20 min. Lastly, 50 μL of stop solution was added to each well, and the absorbance was read immediately at 450 nm. Percentage neutralization was calculated based on the following formula: (1−sample absorbance/negative control absorbance)×100%, with a cut-off value of >20%.

IFN-gγ Levels of secreted IFN-were measured by ELISA using the mouse IFN-(improved) ELISA Kit (Cat #KMC4021; Invitrogen), according to manufacturer instructions. Briefly, 100 μL of pre-diluted serum samples with standard diluent buffer were added to wells. Samples were incubated at room temperature for 2 h, and plates were washed four times with the provided wash buffer.

Next, 100 μL of streptavidin-HRP solution was added to each well, and plates were incubated at room temperature for 30 min.

After washing four times with wash buffer, 100 μL of stabilized chromogenic substrate was added to each well, and plates were incubated at room temperature for 30 min.

Lastly, 100 μL of stopping solution was added to each well, and plates were read at 450 nm.

The results disclosed above show that immunization with a codon-modified pDNA encoding the full-length or 51 subunit of the SARS-CoV-2 S generated potent and robust binding and neutralizing antibodies, as well as IFN-cytokine responses.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A DNA comprising SEQ ID NO: 1, 2, 3 or 4 or a SARS-CoV receptor binding domain thereof.
2. The DNA of claim 1 that is incorporated into a plasmid.
3. The DNA of claim 1 that is S.opt.FL (SEQ ID NO: 2); or that is S1.opt (SEQ ID NO: 4).
4. The DNA of claim 1 that comprises SEQ ID NO: 1.
5. The DNA of claim 1 that comprises the SARS-CoV receptor binding domain of SEQ ID NO: 1.
6. The DNA of claim 1 that lacks all or part of an S2 domain.
7. The DNA of claim 1 that encodes an S protein consisting of an S1 protein.
8. The DNA of claim 1 that lacks at least one of a fusion peptide (FP), a heptad repeat region 1 (HR1), a heptad repeat region 2 (HR2), a transmembrane domain (TM) or a cytoplasmic domain.
9. The DNA of claim 1, further comprising an enhancer-promoter of mammalian origin.
10. The DNA of claim 1, further comprising a cytomegalovirus (CMV) enhancer-promoter of mammalian origin.
11. The DNA of claim 1 that comprises a pcDNA3.1(+) vector.
12. The DNA of claim 1 that is S.opt.FL (SEQ ID NO: 2).
13. The DNA of claim 1 that is S1.opt (SEQ ID NO: 4).
14. A composition comprising the DNA of claim 1 and a pharmaceutically acceptable carrier or adjuvant.
15. The composition of claim 14, wherein said DNA is incorporated into a plasmid.
16. A method for inducing humoral and/or cellular immunity to infection by SARS-CoV-2 comprising administering the DNA of claim 1 to a subject in need thereof.
17. The method of claim 16, wherein the DNA is administered in the form of a plasmid.
18. The method of claim 16, wherein the DNA is administered as three or more intramuscular injections at intervals of one to three weeks.

* * * * *